United States Patent
Hargreaves et al.

(10) Patent No.: US 6,787,556 B1
(45) Date of Patent: Sep. 7, 2004

(54) BENZOIC ACID DERIVATIVES FOR THE TREATMENT OF DIABETES MELLITUS

(75) Inventors: Rodney Brian Hargreaves, Macclesfield (GB); Paul Robert Owen Whittamore, Macclesfield (GB)

(73) Assignee: AstraZeneca AB, Sodertalje (SE)

(*) Notice: Subject to any disclaimer, the term of this patent is extended or adjusted under 35 U.S.C. 154(b) by 0 days.

(21) Appl. No.: 10/048,392

(22) PCT Filed: Aug. 14, 2000

(86) PCT No.: PCT/GB00/03126
§ 371 (c)(1),
(2), (4) Date: Jan. 29, 2002

(87) PCT Pub. No.: WO01/12612
PCT Pub. Date: Feb. 22, 2001

(30) Foreign Application Priority Data

Aug. 18, 1999 (GB) .............................................. 9919413

(51) Int. Cl.[7] .................... A61K 31/41; A61K 31/422; A61K 31/4439; A61K 31/4709
(52) U.S. Cl. ...................... 514/311; 514/340; 514/341; 514/375; 514/381
(58) Field of Search .............................. 514/311, 340, 514/341, 375, 381; 546/118, 176, 268.4, 275.4; 548/222, 253, 306.1, 364.7

(56) References Cited

U.S. PATENT DOCUMENTS 5,234,942 A * 8/1993 Bernstein et al. ........... 514/415

FOREIGN PATENT DOCUMENTS

| EP | 0179619 | 4/1986 |
| WO | 9606822 | 3/1996 |
| WO | 9727190 | 7/1997 |

OTHER PUBLICATIONS

Harper et al., Journal of Medicinal Chemistry, 35(7), 1191–1200, 1992.*
XP–002152390: Journal of Medicinal Chemistry, vol. 35, No. 7, Apr. 3, 1992, pp. 1200–1209; J. S. Sawyer et al.

* cited by examiner

*Primary Examiner*—Fiona T. Powers
(74) *Attorney, Agent, or Firm*—White & Case LLP

(57) ABSTRACT

The present invention relates to the use of certain benzoic acid derivatives of formula (I), as disclosed in the specification, which act as peroxisome proliferator activated receptor (PPAR) agonists, in particular states of insulin resistance including type 2 gamma receptors (PPAR), and so are useful therapeutically in the treatment of diabetes mellitus. Novel pharmaceutical compositions and novel compounds are also defined, together with methods of their production.

3 Claims, No Drawings

BENZOIC ACID DERIVATIVES FOR THE TREATMENT OF DIABETES MELLITUS

The present invention relates to the use of certain benzoic acid derivatives which act as peroxisome proliferator activated receptor (PPAR) agonists, in particular gamma receptors (PPARγ), and so are useful in the treatment of states of insulin resistance, including type 2 diabetes mellitus. Novel pharmaceutical compositions and novel compounds are also defined, together with methods of their production.

Traditionally, therapeutic intervention in type 2 diabetes has had a 'glucocentric focus' dominated by the use of insulin secretogogues e.g. the sulphonylureas and the measurement of glycated haemoglobin (HbA1c) or fasting blood sugar level (FPG) as indices of diabetic control. In the USA, patients with type 2 diabetes are usually treated with diet and, when needed, a sulphonylurea compound. However, it is estimated that approximately 30% of patients initially treated with sulphonylurea agents have a poor response and in the remaining 70%, the subsequent failure rate is approximately 45% per annum. Other estimates put failure rates higher with few patients responding after 10 years therapy. A treatment-related increase in body weight is also experienced with these agents. Prior to the FDA approval of metformin in 1995, the only therapeutic option for type 2 diabetic patients, in whom sulphonylurea therapy had failed, was insulin.

Despite the introduction of newer agents both the incidence and prevalence of type 2 diabetes continues to increase on a global basis. Approximately 16 million people in the USA have diabetes mellitus, 90–95% of whom have type 2 disease. This represents an enormous healthcare burden; estimated in 1998 to be some $98 billion per annum in direct and indirect healthcare costs. Recently, both the ADA and WHO have revised guidelines for the diagnosis of diabetes and classified diabetes more according to aetiology. The threshold for diagnosis (FPG>126 mg/dl) has been lowered and the term 'type 2' is now used to describe mature onset diabetics who have not progressed to insulin therapy. After the ADA implemented these new criteria in 1997, the prevalence of the type 2 disease sector increased by nearly 6 million people in the seven major pharmaceutical markets (France, Germany, Italy, Japan, Spain, UK and USA).

Apart from often mild acute symptoms, type 2 diabetics are also at a considerable risk of developing long term complications of the disease. These include a 4–5 fold higher risk, (compared with non-diabetics), of developing macrovasular disease including CHD and PVD and microvascular complications including retinopathy, nephropathy and neuropathy. In many individuals, overt type 2 diabetes is preceded by a period of reduced insulin sensitivity (insulin resistance), accompanied by a cluster of other cardiovascular risk factors, collectively termed as insulin resistance syndrome (IRS).

It has been estimated that approximately 80% of type 2 diabetics are obese and other co-morbidities of the IRS include: dyslipidemia, hyperinsulineria, raised arterial blood pressure, uricemia and a reduced fibrinolysis. Given the increased global prevalence and incidence of type 2 diabetes and the very high costs of treating the long term complications of the disease there is tremendous interest in the development of agents that delay or prevent the onset of type 2 diabetes and in those that reduce the risk of cardiovascular complications associated with IRS. These activities have lead to the introduction of the thiazolidinedione (TZD) class of insulin sensitisers that improved the dyslipidemia and thus restored the insulin sensitivity leading to improved glycemic control and lower HbA1c levels.

Although the complex interplay between lipids and carbohydrates as metabolic fuels has been recognised for many decades it is only recently, that researchers and clinicians have begun to focus on the importance of dyslipidemia seen in type 2 diabetes. Much has been made of the relative sensitivities of muscle, liver and adipose tissues to insulin and a case for the primacy of insulin resistance in adipose tissue leading to the IRS has been debated. A typical dyslipidemic atherogenic lipoprotein phenotype (referred to as type B) is seen in IRS including frequently in type 2 diabetics, characterised by a modestly raised LDL-C, a more significant increase in VLDL-TG and reduced HDL. Apparently, changes in the physicochemical properties of VLDL-TG particles result in slower plasma clearance rates and in the generation of small dense LDL particles. The latter permeate the vascular endothelium more readily and are more prone to oxidation and glyration and are considered to play a critical role in atherogenesis in large vessels. Although more difficult to measure, improved free fatty acid (IFFA) flux is increasingly considered to play an important role in the IRS affecting metabolic events in muscle, liver, adipose tissue and pancreas.

The first generation TZDs e.g. troglitazone, pioglitazone, rosiglitazone were in clinical development before the putative mechanism of action was discovered and published in 1995 (PPARγ activation). It is clear from experience with these first generation agents that it is difficult to predict from animal pharmacology the safety and efficacy profile these agents will have in the clinic. Thus, knowledge of the putative mechanism of action of this class coupled with concerns regarding safety, offers the opportunity to identify non-TZD activators of PPAR for the treatment of type 2 diabetes and is the subject of this invention. Furthermore, we recognise that agents with a dual action at both α and g PPAR may have additional benefits in reducing diabetic co-morbidities, particularly raised triglycerides. Such agents may be useful in the treatment of type 2 diabetes, the IRS, dyslipidemia and in reducing risk of cardiovascular disease.

Certain heterocyclic amides and their use as leukotriene antagonists is described in EP-A-179619. Additional phenyltetrazole leukotriene $D_4$ receptor antagonists have been described by Sawyer et al., J. Med. Chem. 1992, 35, 7, 1200–1209.

The present invention provides the use of a compound of formula (I)

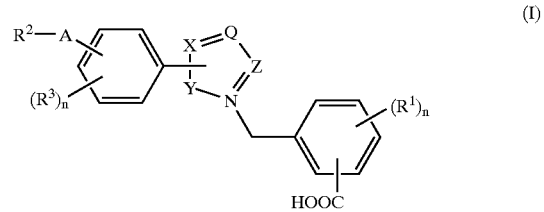

(I)

or a pharmaceutically acceptable salt or ester thereof, in the preparation of a medicament for use in the activation of PPAR, where Q, X, Y and Z are either —$CR^a$=, —$CR^b$=$CR^c$— or —N=; where $R^a$, $R^b$ and $R^c$ are independently selected from hydrogen, halo or a bond, such that together with the nitrogen atom to which Y and Z are attached, they form a five or six-membered aromatic ring;

$R^1$ and $R^3$ are independently selected from $C_{1-3}$alkyl, halo, halo$C_{1-3}$alkyl, $C_{1-3}$alkoxy, or halo$C_{1-3}$alkoxy;

n and m are independently selected from 0, 1 or 2;

A is an alkylene, alkenylene or alkynylene chain optionally interposed by a heteroatom; and $R^2$ is an optionally substituted aryl, optionally substituted heterocyclyl or optionally substituted cycloalkyl moiety.

As used herein, the term "hydrocarbyl" refers to alkyl, alkenyl, alkynyl, aryl, aralkyl, cycloalkyl, cycloalkenyl or cycloalkynyl groups.

As used herein the term "heterocyclyl" refers to single or fused ring structures which, unless stated otherwise, may be aromatic or non-aromatic in nature and which suitably contain from 2 to 20 ring atoms, suitably from 5 to 8 ring atoms, at least one of which and suitably up to four of which are heteroatoms. The term "heteroatom" includes oxygen, sulphur and nitrogen. Where a heteroatom is nitrogen, it will be further substituted for example by hydrogen or an alkyl group.

In this specification the term "aryl" refers to phenyl, biphenyl and naphthyl.

The term "heterocyclyl" includes aromatic or non-aromatic rings, for example containing from 4 to 20, Examples of such groups include furyl, thienyl, pyrrolyl, pyrrolidinyl, imidazolyl, triazolyl, thiazolyl, tetrazolyl, oxazolyl isoxazolyl, pyrazolyl, pyridyl, pyrimidinyl, pyrazinyl, pyridazinyl, triazinyl, quinolinyl, isoquinolinyl, quinoxalinyl, benzothiazolyl, benzoxazolyl, benzothienyl or benzofuryl.

"Heteroaryl" refers to those groups described above which have an aromatic character.

In this specification the term "alkyl" when used either alone or as a suffix includes straight chain or branched structures. These groups may contain up to 10, preferably up to 6 and more preferably up to 4 carbon atoms. Similarly the terms "alkenyl" and "alkynyl" refer to unsaturated straight or branched structures containing for example from 2 to 10, preferably from 2 to 6 carbon atoms. Cyclic moieties such as cycloalkyl, cycloalkenyl and cycloalkynyl are similar in nature but have at least 3 carbon atoms, suitably from 3 to 20 carbon atoms and preferably from 3 to 7 carbon atoms. Terms such as "alkoxy" comprise alkyl groups as is understood in the art.

The term "halo" includes fluoro, chloro, bromo and iodo. References to aryl groups include aromatic carbocylic groups such as phenyl and naphthyl.

Preferably, the group comprising —Y—X—Q—Z— and the nitrogen to which it is attached forms a 5-membered aromatic ring. Preferably however, any other heteroatoms in this ring are also nitrogen. Examples of such groups include tetrazolyl, triazolyl, pyrazolyl, imidazolyl pyrrolyl, pyridyl, pyridazinyl or pyrimidinyl, and preferably tetrazolyl, pyrazolyl or imidazolyl.

Thus examples of the group formed by —Y—X—Q—Z and the nitrogen atom to which they are attached include the following groups (i) to (vii);

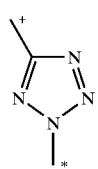
(i)

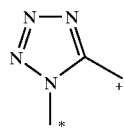
(ii)

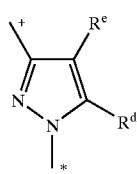
(iii)

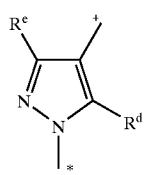
(iv)

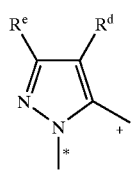
(v)

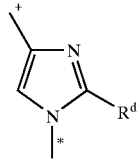
(vi)

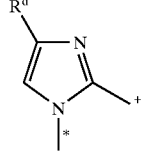
(vii)

where $R^d$ and $R^e$ are independently selected from hydrogen or halo, preferably hydrogen, * indicates the nitrogen atom illustrated in formula (I) and + indicates the point of attachment to he group —A—$R^2$.

Suitable optional substituents for the group $R^2$ include alkyl, alkenyl, alkynyl, aryl, heterocyclyl, alkoxy, aralkyl, cycloalkyl, cycloalkenyl cycloalkynyl, halo, cyano, nitro, $C(O)_aR^8$, $OR^8$, $S(O)_bR^8$, $NR^9R^{10}$, $C(O)NR^9R^{10}$, $OC(O)NR^9R^{10}$, $NR^8C(O)_aR^9$, $NR^8CONR^9R^{10}$, $N=CR^9R^{10}$, $S(O)_bNR^9R^{10}$ or $NR^8S(O)_bR^{10}$ where $R^8$, $R^9$ and $R^{10}$ are independently selected from hydrogen, alkyl, alkenyl, alkynyl, aryl, heterocyclyl, alkoxy, aralkyl, cycloalkyl, cycloalkenyl or cycloalkynyl, any of which may themselves be optionally substituted, a is 1 or 2 and b is 0, 1, 2 or 3.

Suitable optional substituents for alkyl, alkenyl, alkynyl, aryl, heterocyclyl, alkoxy, aralkyl, cycloalkyl, cycloalkenyl or cycloalkynyl groups $R^8$, $R^9$ and $R^{10}$ include halo, nitro cyano, alkanoyl such as acetyl, oxo, carboxy or salts or esters thereof; alkoxy such as methoxy, ethoxy or propoxy, aryloxy such as phenoxy, thioalkyl such as thiomethyl, thioethyl or thiopropyl, sulphate, haloalkyl such as tifluoromethyl, aryl such as phenyl, carbamate, amino, mono- or di-alkyl amino such as methylamino or di-methylamino. Aryl, heterocyclyl or aralkyl groups $R^8$, $R^9$ and $R^{10}$ may further be substituted by alkyl, alkenyl or alkynyl groups suitably having from 1 to 4 carbon atoms.

In particular $R^2$ is an optionally substituted heterocyclic group, such as pyridyl, indole, quinoline, isoquinoline, benzimidazoline, benzpyrazole.

Preferred optional substituents for such groups include alkyl, aryl and groups of formula $NR^8C(O)_aR^9$ where $R^8$, $R^9$ and a are as defined above.

Where $R^2$ is substituted by a group $NR^8C(O)_nR^9$, $R^8$ is preferably hydrogen, whilst $R^9$ is preferably alkyl, such as $C_{1-6}$ alkyl, or cycloalkyl, such as cyclopentyl.

Suitably $R^3$ is alkoxy in particular methoxy or halo such as bromo. Preferably m is 0 or 1.

Suitable groups for A include —$(CH_2)_p$—, —$O(CH_2)_p$—, —$(CH_2)_pO$— —$(CH_2)_p$—, —$NR^5(CH_2)_p$— or —$(CH_2)_p NR^5$— where p is an integer of 1 to 3 and is preferably 1 and $R^5$ is hydrogen or alkyl, in particular $C_{1-6}$ alkyl such as methyl.

Preferably l is 1.

Preferably n is 0 or 1. Ideally n is 0.

Preferably m is 0 or 1. Ideally m is 0.

Preferably $R^1$ is selected from $C_{1-3}$alkyl, halo, halo$C_{1-3}$alkyl and $C_{1-3}$alkoxy.

In the compounds of formula (I), the carboxylic acid group is suitably at the ortho position on the benzyl ring. Thus preferred compounds of formula (I) are compounds of formula (II)

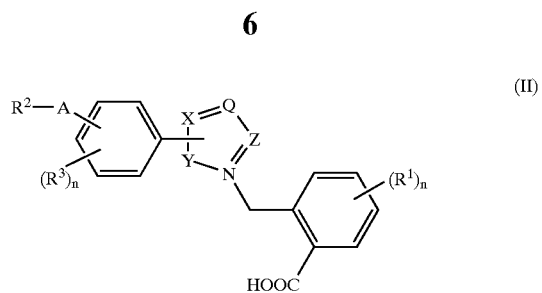

(II)

where X, Y, Z, Q, A, $R^1$, $R^2$, $R^3$, m and n are as defined in relation to formula (I).

Furthermore, in compounds of formula (I), the group $R^2$—A— is suitably in the para position relative to the ring formed by the Y—X—Q—Z— and the nitrogen atom to which they are attached. Thus further preferred compounds of formula (I) are compounds of formula (III)

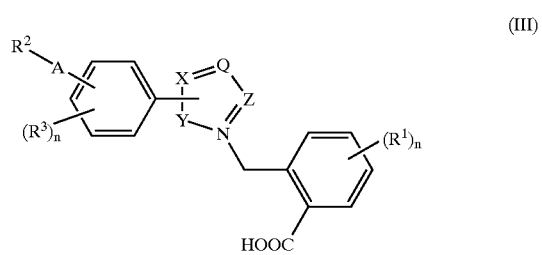

(III)

where X, Y, Z, Q, A, $R^1$, $R^2$, $R^3$, m and n are as defined in relation to formula (I).

Particular examples of compounds of formula (I) include the compounds listed in Table 1 and esters thereof.

TABLE 1

| Compound No | Structure |
|---|---|
| 1 | 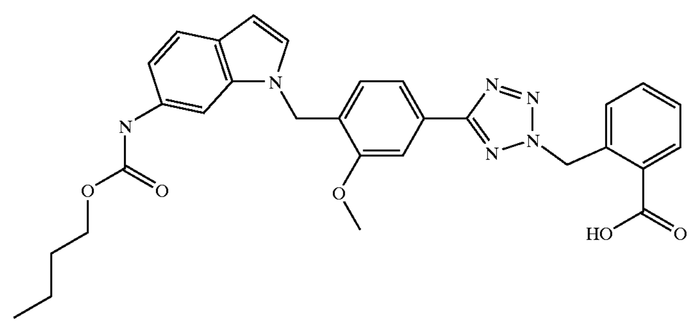 |
| 2 | 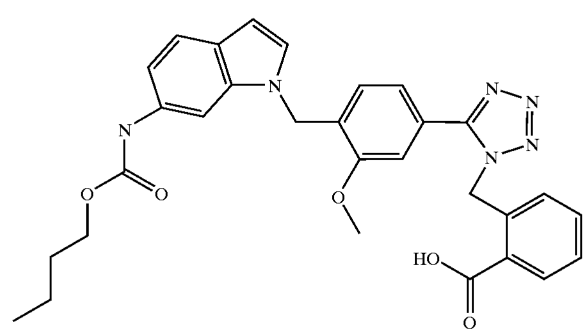 |

TABLE 1-continued

| Compound No | Structure |
|---|---|
| 3 | 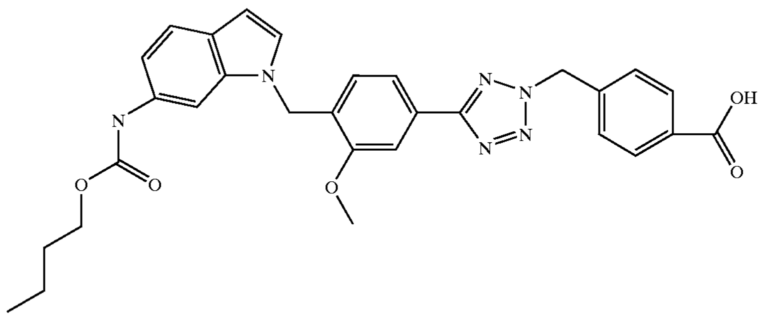 |
| 4 | 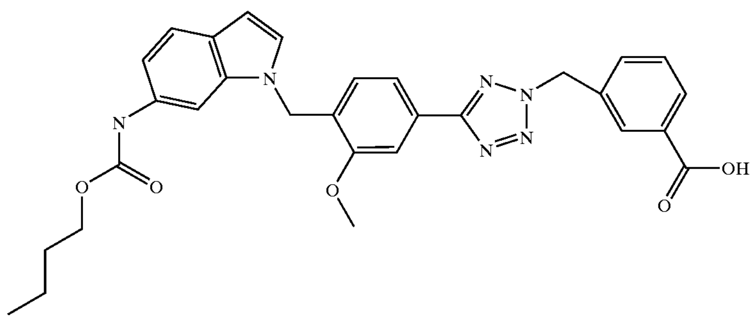 |
| 5 | 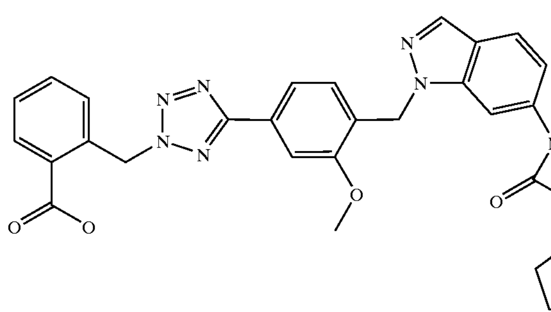 |
| 6 | 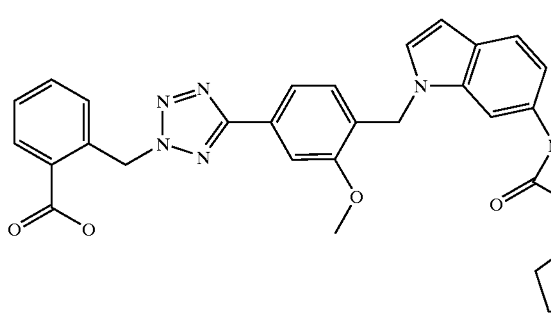 |
| 7 | 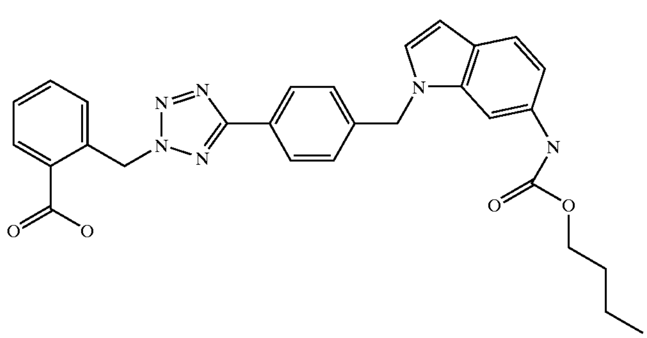 |

TABLE 1-continued

| Compound No | Structure |
|---|---|
| 8 | 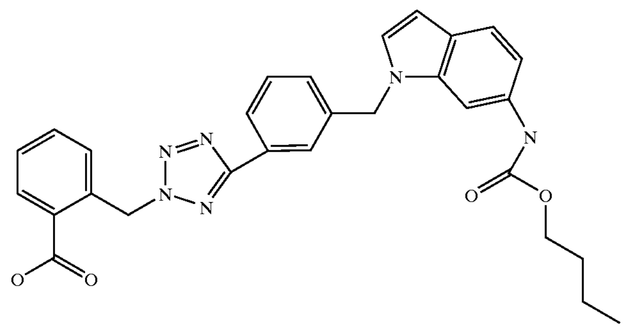 |
| 9 | 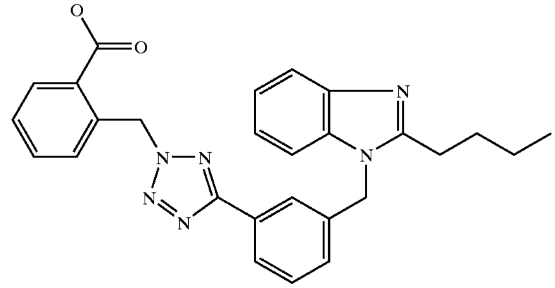 |
| 10 | 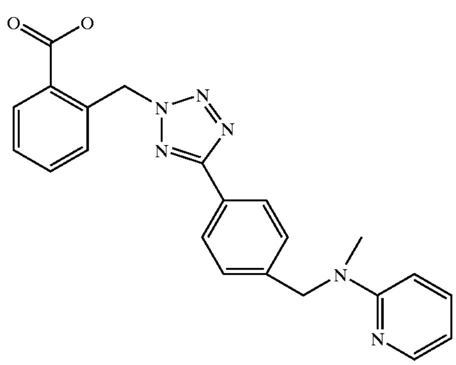 |
| 11 | 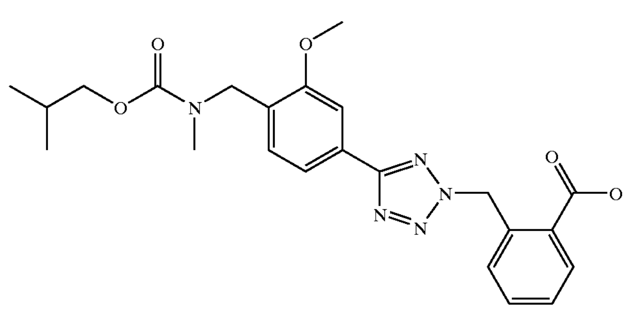 |
| 12 | 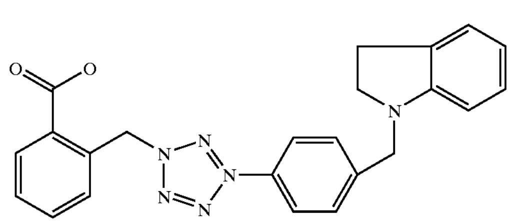 |

TABLE 1-continued

| Compound No | Structure |
|---|---|
| 13 | 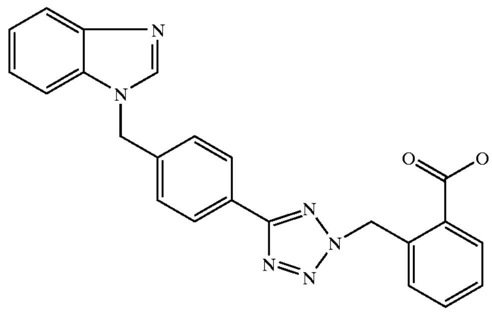 |
| 14 | 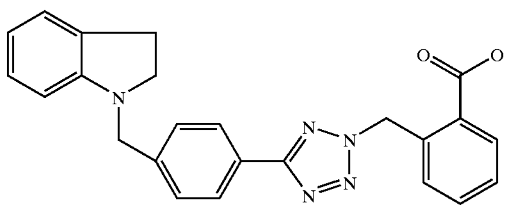 |
| 15 | 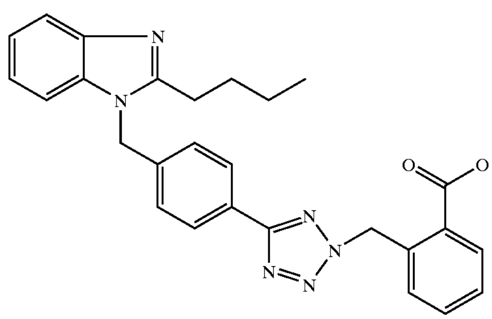 |
| 16 | 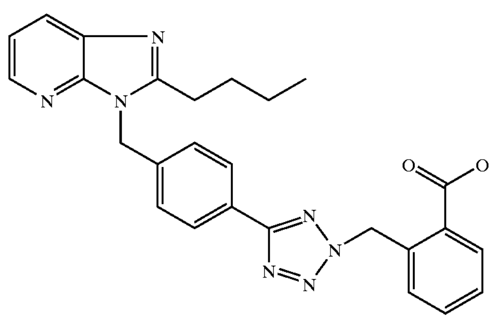 |
| 17 | 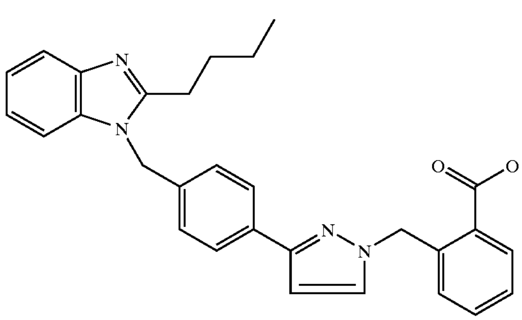 |

TABLE 1-continued

| Compound No | Structure |
|---|---|
| 18 | 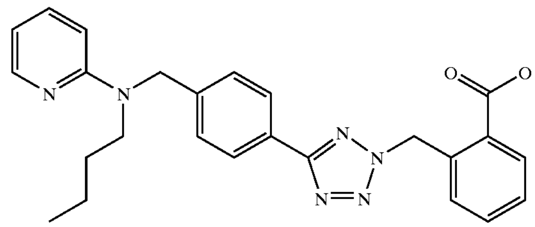 |
| 19 | 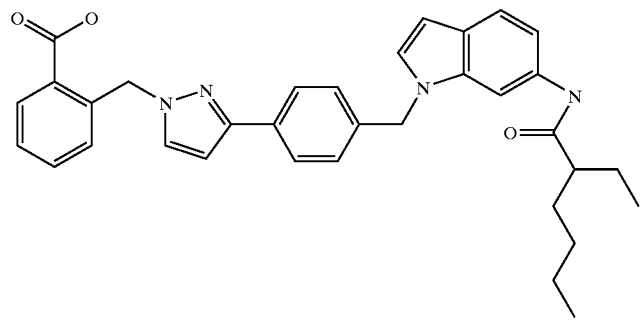 |
| 20 | 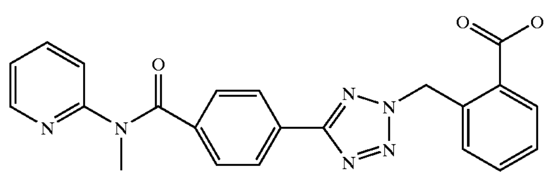 |
| 21 | 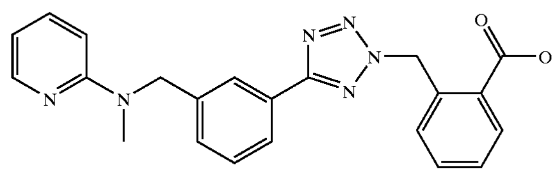 |
| 22 | 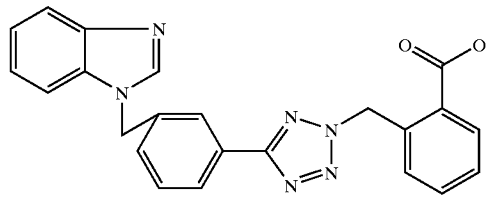 |
| 23 | 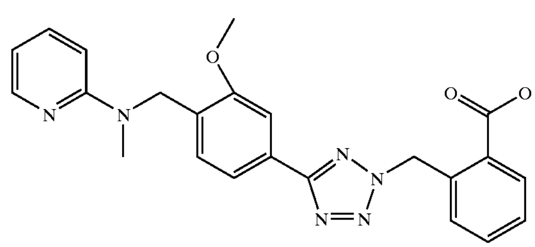 |

TABLE 1-continued

| Compound No | Structure |
| --- | --- |
| 24 | 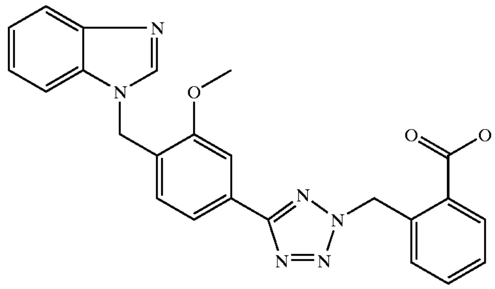 |
| 25 | 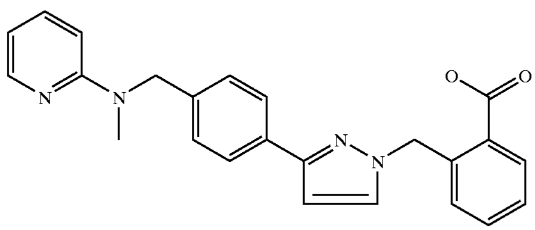 |
| 26 | 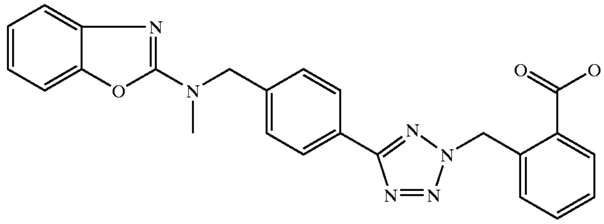 |
| 27 | 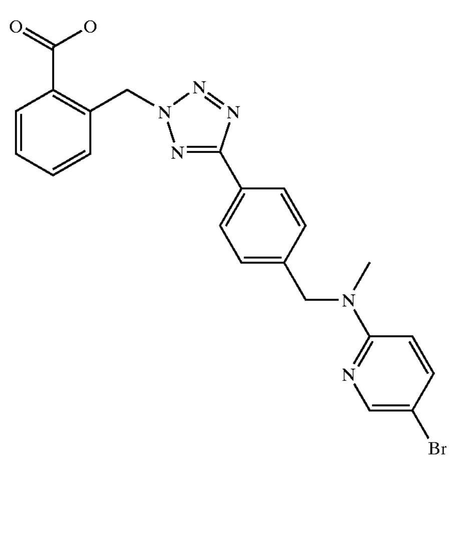 |

TABLE 1-continued

| Compound No | Structure |
|---|---|
| 28 | 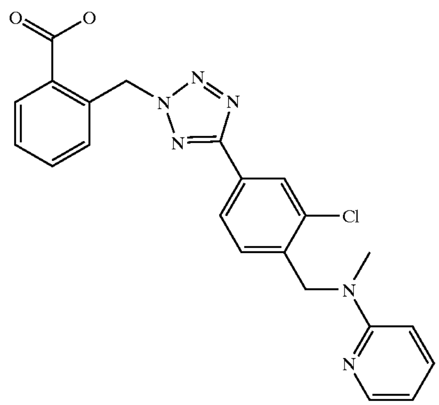 |
| 29 | 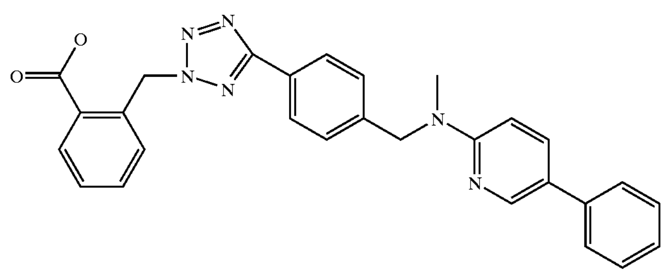 |
| 30 | 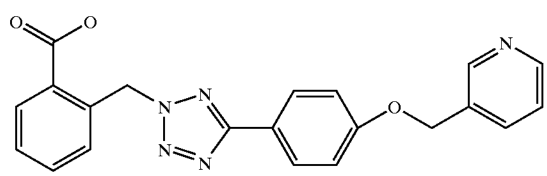 |
| 31 | 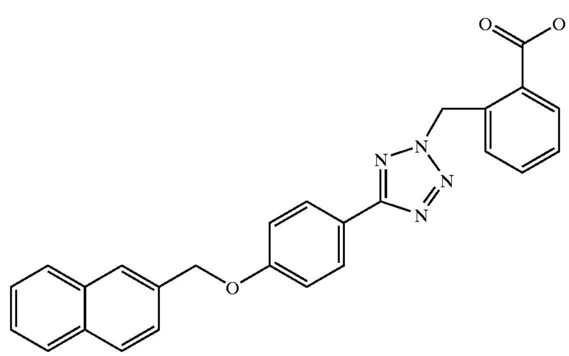 |
| 32 | 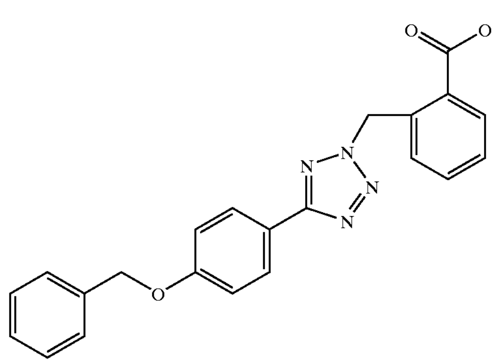 |

TABLE 1-continued
| Compound No | Structure |
|---|---|
| 33 | 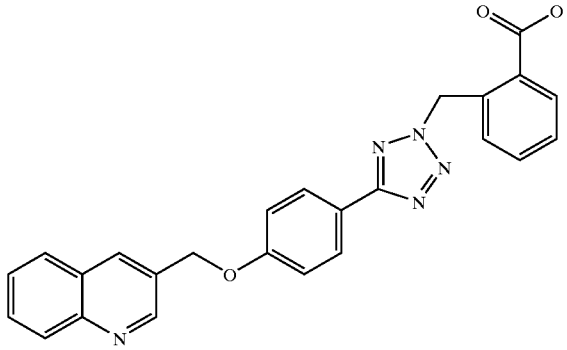 |
| 34 | 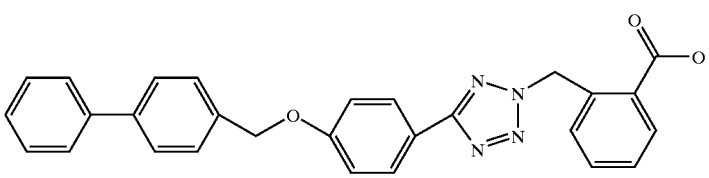 |
| 35 | 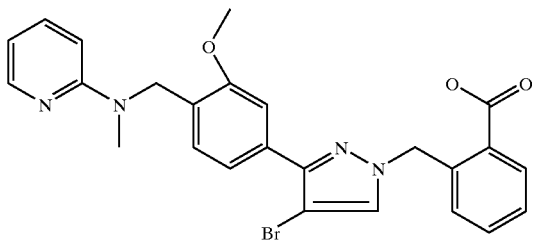 |
| 36 | 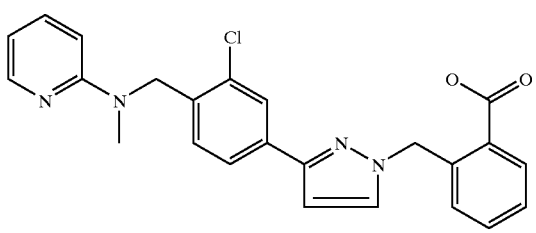 |
| 37 | 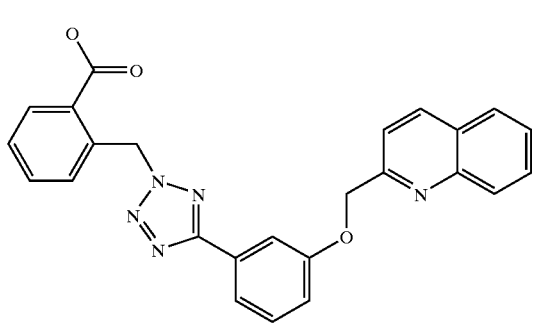 |

TABLE 1-continued

| Compound No | Structure |
| --- | --- |
| 38 | 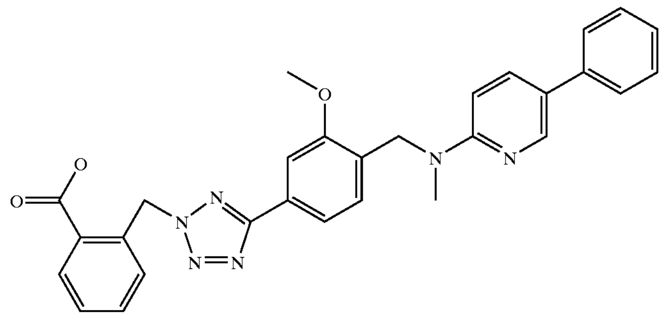 |
| 39 | 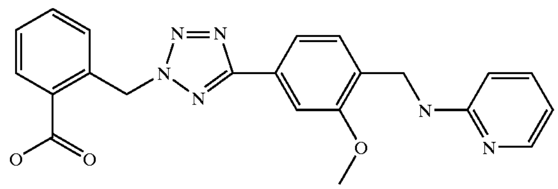 |
| 40 | 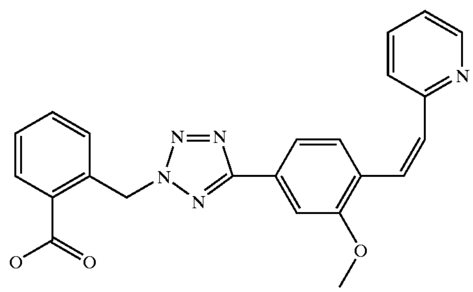 |
| 41 | 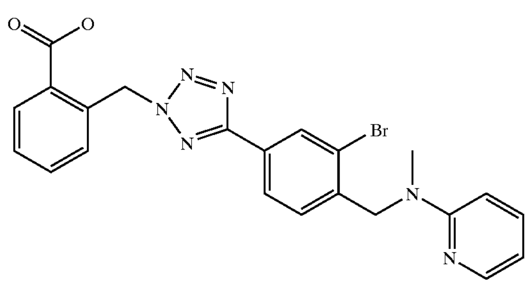 |
| 42 | 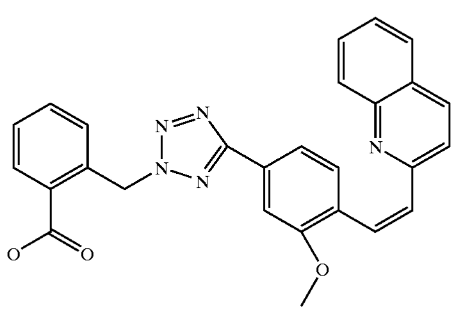 |

TABLE 1-continued
| Compound No | Structure |
|---|---|
| 43 | 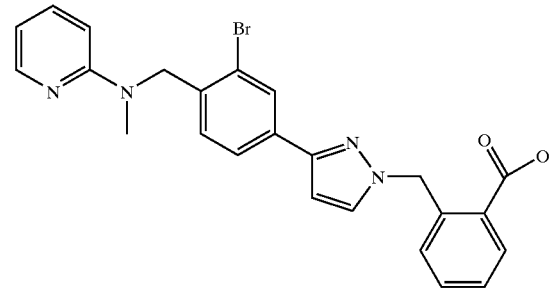 |
| 44 | 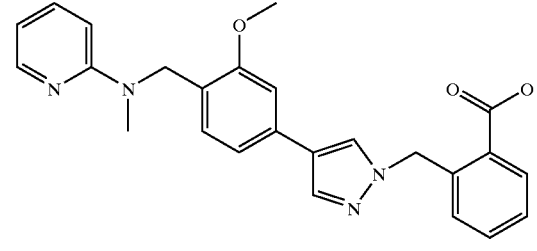 |
| 45 | 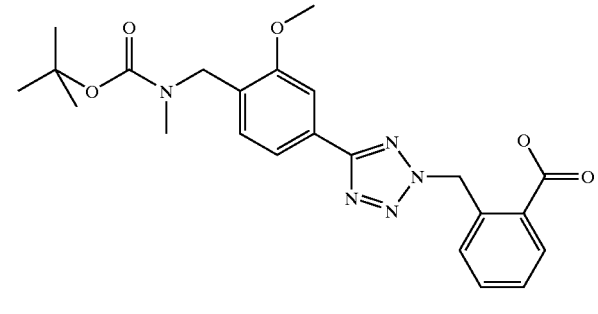 |
| 46 | 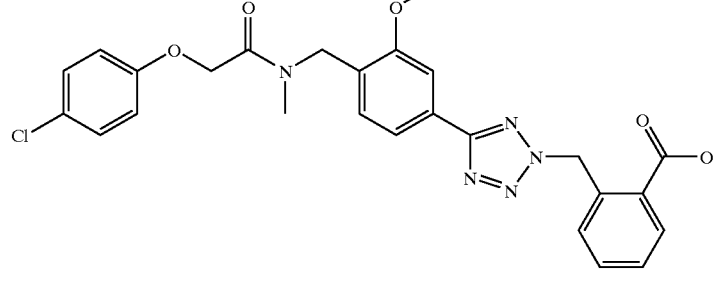 |
| 47 | 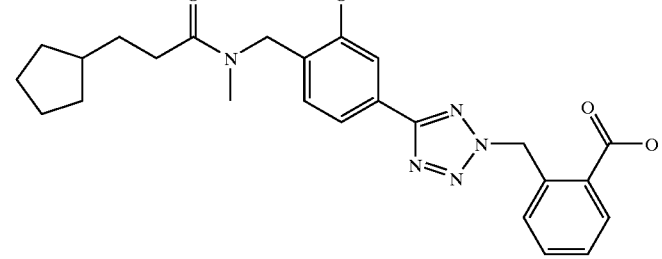 |

The use of certain compounds of formula (I) in any medical application has not been described before. Hence, in a further aspect the invention provides the use of these particular compounds as medicaments, and pharmaceutical compositions containing them.

Thus the invention provides a compound of formula (IA) which comprises a compound of formula (I) as defined above, provided that (a) where Q, X, Y and Z together with the nitrogen atom to which they are attached from a group of formula (i) above, when the group $R^2$—A— is attached at the meta position on the phenylene ring, and A is ethylene, —O(CH$_2$)— or —(CH$_2$)S—, $R^2$ is other than quinoline optionally substituted by chloro, or unsubstituted benzothiazol; or (b) where Q, X, Y and Z together with the nitrogen atom to which they are attached from a group of formula (i) above, when $R^3$ is methoxy, m is 1, the group $R^2$—A— is attached at the para position on the phenylene ring, and A is —(CH$_2$)—, $R^2$ is other than indole substituted by —NR$^8$C(O)$_2$R$^9$ where $R^8$ is hydrogen and $R^9$ is alkyl; or for use a medicament.

Suitable compounds of formula (IA) are compounds where Q, X, Y and Z together with the nitrogen atom to which they are attached form a group heterocyclic group other than tetrazole.

In addition, the invention provides a pharmaceutical composition comprising a compound of formula (IA) in combination with a pharmaceutically acceptable carrier.

Preferred groups within formula (IA) are as set out above in relation to formula (I).

Compounds of formula (IA) are novel and these form a further aspect of the invention.

Compounds of formula (I) are either known compounds or they may be prepared using conventional methods. For example, benzoic acid, 2-[[5-[3-(2-quinolinylmethoxy) phenyl]-2H-tetrazol-2-yl]methyl]-(9CI) (Compound 37 in Table 1) and its preparation is described by Sawyer, J. Scott; Baldwin, Ronald F.; Rinkema, Lynn E.; Roman, Carlos R.; Fleisch, Jerome H. Optimization of the quinoline and substituted benzyl moieties of a series of phenyltetrazole leukotriene D4 receptor antagonists. J. Med. Chem. (1992), 35(7), 1200–9. CODEN: JMCMAR; ISSN: 0022-2623. CAN 116:174064 CAPLUS.

In particular however, compounds of formula (I) may be prepared by reacting a compound of formula (IV)

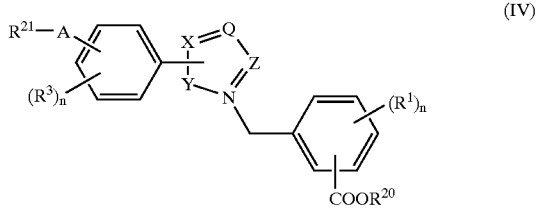

(IV)

where X, Y, Z, Q, A, $R^1$, m and n are as defined in relation to formula (I); $R^{20}$ completes an ester group, and so is, for example an alkyl group, $R^{21}$ is a leaving group; with a compound of formula (V)

$R^2$—H          (V)

where $R^2$ is as defined in relation to formula (I) or a precursor thereof, and thereafter, if desired, removing the group $R^{20}$ to form the corresponding carboxylic acid.

The reaction is suitably effected in an organic solvent such as dimethylformamide (DMF) in the presence of a base such as an alkali metal carbonate such as potassium carbonate. Suitable leaving groups for $R^{21}$ include halo such as bromo, mesylate and tosylate.

Any de-esterification is suitably carried out by addition of a base such as an alkali metal hydroxide such as lithium hydroxide or sodium hydroxide in the presence of an organic solvent such as an alcohol for instance, methanol, or trifluoroacetic acid (TFA).

Compounds of formula (IV) are suitably prepared by reacting a compound of formula (VI)

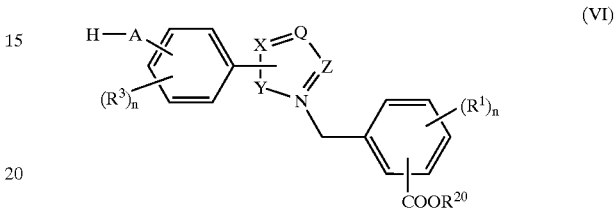

(VI)

where X, Y, Z, Q, A, $R^1$, $R^3$ m and n are as defined in relation to formula (I) and $R^{20}$ is as defined in relation to formula (V) above, with an appropriate leaving group reagent. For example, where $R^{21}$ is a halogen group, the compound will be reacted with a halogenating agent such as N-bromosuccinimide in the presence of a base such as azoisobutyronitrile (AIBN).

Compounds of formula (VI) where A includes for example heteroatoms spaced from the ring such as nitrogen, may be prepared by reacting a compound of formula (VIA)

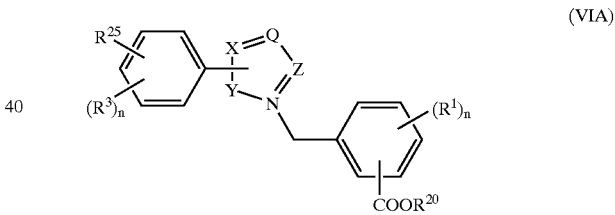

(VIA)

where $R^{25}$ is an alkyl group substituted by a leaving group, with an appropriate primary or secondary amine in particular a monoalkylamine such as methylamine. Suitable leaving group substituents for $R^{25}$ include those listed above for $R^{21}$. The reaction is suitably effected in an organic solvent such as an alcohol like ethanol at moderate or depressed temperatures, for example of from −20° C. to ambient temperature, and conveniently at about 0° C.

Compounds of formula (VI) are suitably prepared by reacting a compound of formula (VII)

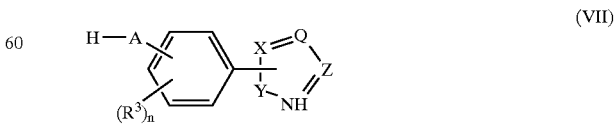

(VII)

where X, Y, Z, Q, A, $R^3$ and n are as defined in relation to formula (I); with a compound of formula (VIII)

(VIII)

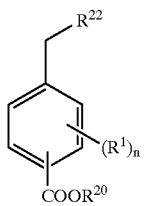

where $R^1$ and n are as defined in relation to formula (I), $R^{20}$ is as defined in relation to formula (VI) and $R^{22}$ is a leaving group such as halo, and in particular bromo. The reaction is suitably effected in an organic solvent such as acetone or DMF, in the presence of a base such as an alkali metal carbonate for instance potassium carbonate.

Compounds of formula (VII) will be prepared using various methods depending upon the precise nature of the heterocyclic ring completed by —Y—X—Q—Z—. These methods would be apparent to the chemist and can be based upon literature references. For example, where —Y—X—Q—Z— together with the nitrogen atom to which they are attached form a tetrazole ring, these may be prepared by reacting a compound of formula (IX)

(IX)

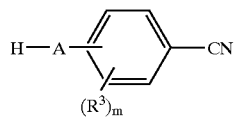

where $R^3$, m and A are as defined in relation to formula (I), with an azide such as sodium azide or n-tributyltin azide (n-Bu$_3$SnN$_3$). The reaction may be effected in a solvent such as N-methylpyrrolidine (NMP) in the presence of abase such as triethylamine hydrochloride where necessary.

Such a reaction will result in the production of a compound of formula (X)

(X)

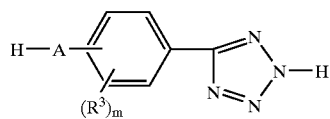

where $R^3$, m and A are as defined in relation to formula (I). This may be converted to other compounds of formula (VII) such as pyrazoles by heating the compound with an alkene of formula (XI)

(XI)

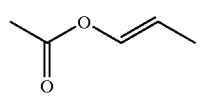

in the presence of a condensation reagent such as Hg(OAc)$_2$, and thereafter rearranging the product of formula (XII)

(XII)

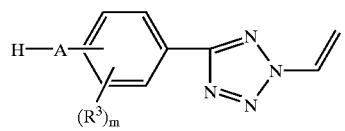

where $R^3$, m and A are as defined in relation to formula (I) for example by heating to temperatures of from 150 to 200° C., in the presence of dichlorobenzene (DCB) to yield the corresponding pyrazole of formula (XIII)

(XIII)

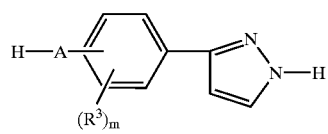

Alternatively, pyrazoles can be prepared by reacting a compound of formula Compounds of formula (VIII) and (IX) are either known compounds of they can be prepared from known compounds using conventional methods.

Alternatively, compounds of formula (I) may be prepared by reacting a compound of formula (XIV)

(XIV)

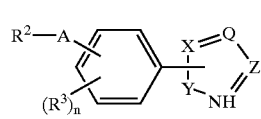

where X, Y, Z, Q, A, $R^2$, $R^3$, m and n are as defined in relation to formula (I); with a compound of formula (VIII) as defined above. The reaction is suitably effected under conditions similar to those described for the reaction between compounds of formula (VII) and (VIII).

Compounds of formula (XIV) may be prepared by treating a compound of formula (XV)

(XV)

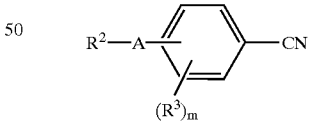

where $R^2$, $R^3$, A and m are as defined in relation to formula (I) in a similar manner and with similar reagents to that described above in relation to the compounds of formula (IX).

In yet a further alternative, compounds of formula (I) where A contains a nitrogen heteroatom may be prepared by reduction of the corresponding amide. Thus for example, compounds of formula (I) where A is a group —NR$^{26}$CH$_2$— where $R^{26}$ is hydrogen or alkyl may be prepared by reduction of a compound of formula (XVI)

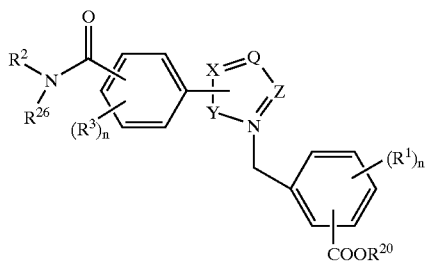
(XVI)

where X, Y, Q, Z, $R^1$, $R^2$, $R^3$, m and n are as defined in relation to formula (I), $R^{20}$ is as defined in relation to formula (IV) and $R^{26}$ is hydrogen or alkyl such as methyl, and thereafter, if necessary or desired, removing any protecting groups $R^{20}$ for example by deesterification. Suitably the reaction is effected using a reducing agent such as trichlorosilane in an organic solvent such as dichloromethane. Elevated temperatures, conveniently the reflux temperature of the solvent are suitably employed. Optionally the reaction is effected in an inert atmosphere, for example in an argon atmosphere. Compounds of formula (XVI) are suitably prepared by reacting a compound of formula (XVII)

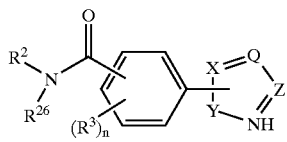
(XVII)

where X, Y, Q, Z, $R^2$, $R^3$ and m are as defined in relation to formula (I), $R^{26}$ is as defined in relation to formula (XVI) with a compound of formula (VIII) as defined above, under conditions similar to those described for the reaction between compounds of formula (VII) and (VIII).

Compounds of formula (XVII) may be obtained by treatment of a compound of formula (XVIII)

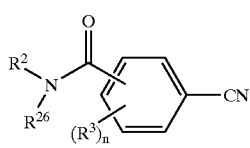
(XVIII)

where $R^2$, $R^3$ and m are as defined in relation to formula (I) and $R^{26}$ is as defined in relation to formula (XVI) as described above for the treatment of compounds of formula (IX).

Compounds of formula (XVIII) are suitable prepared by reacting a compound of formula (XIX)

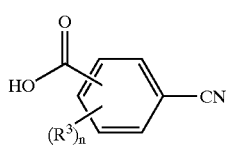
(XIX)

where $R^3$ and m are as defined above, with an amine of formula (XX)

(XX)

where $R^2$ and $R^{26}$ are as defined above, using conditions which would be well known in the art.

Where A contains an oxygen atom directly bonded to the phenyl ring, compounds may be prepared by derivatisation of the corresponding hydroxy compound. Thus compounds of formula (XXI)

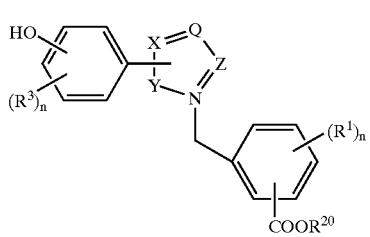
(XXI)

where X, Y, Q, Z, $R^2$, $R^3$, n and m are as defined in relation to formula (I), $R^{20}$ is as defined in relation to formula (V), with a compound of formula (XXII)

$$R^{27}-R^{28}$$ (XXII)

where $R^{27}$ is a group such that —$OR^{27}$ is a group —A—$R^2$ as defined in relation to formula (I) or a precursor thereof, and $R^{28}$ is a leaving group such as halogen, mesylate or tosylate. Reaction conditions are suitably similar to those described above in relation to the reaction of compounds of formula (IV) and (V).

Compounds of formula (XIX) and (XX) are known compounds or they can be prepared from known compounds by conventional methods.

In yet a further alternative method, the compounds of the invention may be prepared by reacting a compound of formula (XXIII)

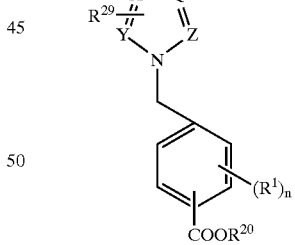
(XXIII)

where X, Y, Q, Z, $R^1$ and n are as defined in relation to formula (I), $R^{20}$ is as defined in relation to formula (V) and $R^{29}$ is a leaving group, with a compound of formula (XXIV)

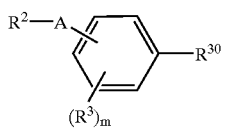
(XXIV)

where $R^2$, $R^3$, A and m are as defined in relation to formula (I) and $R^{30}$ is a boronate derivative,

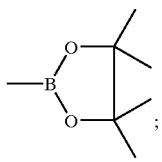

for example of formula —B(OH)$_2$ or ; and thereafter if desired or necessary removing any protecting group R$^{20}$. Suitable leaving groups for R$^{29}$ include halogen such as iodine. The reaction is suitably effected under an inert atmosphere for example of argon in an organic solvent such as dimethyl formamide in the presence of a palladium catalyst such as palladium chloride. The reaction is suitably effected at moderated temperatures, for example from 20–100° C., suitably at about 60° C.

Compounds of formula (XXIII) may be prepared by reacting a compound of formula (XXV)

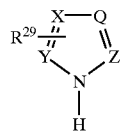

(XXV)

where X, Y, Q and Z are as defined in relation to formula (I) and R$^{29}$ is as defined in relation to formula (XXIII) with a compound of formula (VIII) as defined above. Reaction conditions are suitably similar to those described in relation to the reaction between compounds of formula (VII) and (VIII).

Compounds of formula (XXIV) are suitably prepared by reacting a compound of formula (XXVI)

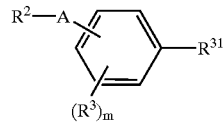

(XXVI)

wherein R$^2$, R$^3$, A and m are as defined in relation to formula (I) and R$^{31}$ is a halogen group such as iodine, with appropriate diboron compound as illustrated hereinafter.

Compounds of formula (XXV) and (XXVI) are either known compounds or they can be prepared from known compounds by conventional methods.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal track, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxyethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil or a mineral oil such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Suppository formulations may be prepared by mixing the active ingredient with a suitable non-irritating excipient which is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedure well known in the art.

Compositions for administration by insufflation may be in the form of a finely divided. powder containing particles of average diameter of, for example, 30µ or much less, the powder itself comprising either active ingredient alone or diluted with one or more physiologically acceptable carriers such as lactose. The powder for insufflation is then conveniently retained in a capsule containing, for example, 1 to 50 mg of active ingredient for use with a turbo-inhaler device, such as is used for insufflation of the known agent sodium cromoglycate.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on Formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

The size of the dose for therapeutic or prophylactic purposes of a compound of the Formula I will naturally vary according to the nature and severity of the conditions, the age and sex of the animal or patient and the route of administration, according to well known principles of medicine. In particular, compounds of formula (I) and compositions containing them will be used in the treatment of diabetes.

Thus in yet a further aspect, the invention provides a method of treating diabetes which comprises administering to a patient an effective amount of a compound of formula (I) as defined above.

The invention will now be particularly described by way of example.

EXAMPLES

Example 1

Preparation of 2-(2-carboxybenzyl)-5-[3-methoxy-4-(N-methyl-N-2-pyridyl)aminomethyl] phenyltetrazole (Compound 23 in Table 1)

Step 1
5-(3-methoxy-4-methyl)phenyltetrazole

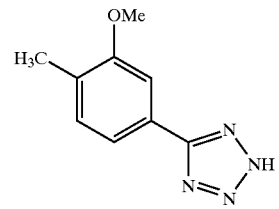

A mixture of 3-methoxy-4-methylbenzonitrile (1.47 g, 10 mmol), triethylamine hydrochloride (2.1 g, 15 mmol) and sodium azide (2.0 g, 30 mmol) in 1-methyl-2-pyrrolidinone (20 ml) was stirred at 150° C. for 3 hours. The mixture was cooled, diluted with water (30 ml) and acidified with 2M hydrochloric acid (30 ml). The resulting precipitate was collected by filtration, washed with water and dried to afford the required product (1.9 g). NMR d ($d_6$-DMSO) 2.2 (3H, s), 3.88 (3H, s), 7.35 (1H, d), 7.55 (2H, m); MS[MH]$^+$ 191

Step 2
2-(2-carbomethoxybenzyl)-5-(3-methoxy-4-methyl)phenyltetrazole

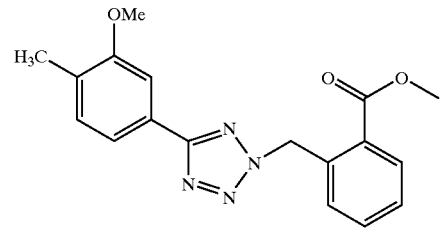

A mixture of 5-(3-methoxy-4-methyl)phenyltetrazole (760 mg, 4 mmol), 2-carbomethoxybenzyl-bromide (788 mg, 4 mmol), potassium carbonate (1.38 g, 10 mmol) and potassium iodide (20 mg) in acetone (50 ml) was stirred under reflux for 16 hours. The acetone was evaporated under reduced pressure and the residue was partitioned between water and ethyl acetate. The organic layer was washed with water, dried over anhydrous magnesium sulphate, filtered and evaporated to a gum. This was purified by flash column chromatography on a Varian 20 g silica megabondelut column eluting with 5% v/v to 20% v/v ethyl acetate in isohexane to obtain the title compound (700 mg). NMR d (d$_6$-DMSO) 2.2 (3H, s), 3.8 (3H, s), 3.84 (3H, s), 6.25 (2H, s), 7.25 (2H, d), 7.5 (3H, m), 7.62 (1H, t), 7.97 (1H, d); MS[MH]$^+$ 339.

Step 3
2-(2-carbomethoxybenzyl)-5-(4-bromomethyl-3-methoxy)phenyltetrazole

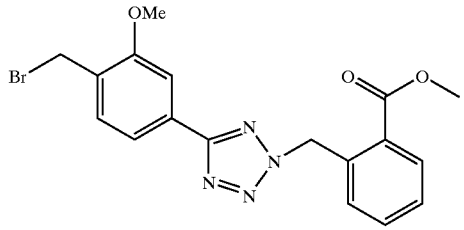

A mixture of 2-(2-carbomethoxybenzyl)-5-(3-methoxy-4-methyl)phenyltetrazole (676 mg, 2 mmol), N-bromosuccinimide (390 mg, 2.2 mmol) and benzoyl peroxide (30 mg) in carbon tetrachloride (30 ml) was stirred under reflux for 3 hours. The reaction mixture was cooled to ambient temperature and washed with water (2×30 ml). The organic extract was dried over anhydrous magnesium sulphate, filtered and concentrated under reduced pressure to leave the title compound (880 mg). NMR d (d$_6$-DMSO) 3.8 (3H, s), 3.95 (3H, s), 4.63 (2H, s), 6.5 (2H, s), 7.3 (1H, t), 7.6 (5H, m), 7.95 (1H, d); MS[MH]+ 417/419.

Step 4
2-(2-carbomethoxybenzyl)-5-[3-methoxy-4-(N-methyl-N-2-pyridyl)aminomethyl]phenyltetrazole

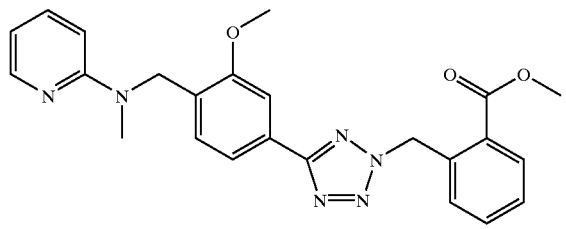

A mixture of 2-(2-carbomethoxybenzyl)-5-(4-bromomethyl-3-methoxy)phenyltetrazole (209 mg, 0.5 mmol), 2-methylaminopyridine (108 mg, 1.0 mmol), potassium carbonate (280 mg, 2.0 mmol) and potassium iodide (84 mg, 0.5 mmol) in N,N-dimethylacetamide (10 ml) was stirred at ambient temperature for 16 hours. The reaction mixture was diluted with water (50 ml) and extracted with ethyl acetate. The organic extract was washed with water, dried over anhydrous magnesium sulphate, filtered and the solvent removed under reduced pressure. The residue was purified by flash column chromatography on Varian 20 g silica megabondelut column eluting with 10% v/v to 20% v/v ethyl acetate in isohexane to obtain the title compound (90 mg). MS[MH]$^+$ 445.

Step 5

Compound 23

A mixture of 2-(2-carbomethoxybenzyl)-5-[3-methoxy-4-(N-methyl-N-2-pyridyl)aminomethyl]phenyltetrazole (90 mg, 0.2 mmol) and 1M aqueous lithium hydroxide (1 ml, 1 mmol) in methanol (10 ml) was stirred under reflux for 1 hour. The mixture was cooled, diluted with water (30 ml) and acidified with 2M hydrochloric acid (10 ml). The resulting mixture was washed with ethyl acetate and the aqueous layer was evaporated under reduced pressure to leave the product as the hydrochloride salt (20 mg). NMR d (d$_6$-DMSO) 3.19 (3H, s), 3.89 (3H, s), 4.82 (2H, s), 6.3 (2H, s), 6.9 (1H, t), 7.2 (2H, t), 7.27 (1H, d), 7.52 (1H, t), 7.6 (3H, m), 8.0 (3H, m); MS[MH]$^+$ 431

Example 2

Using the appropriate cyanotoluene in place of 2-methoxy-4-cyanotoluene and the appropriate amine in place of 2-methylaminopyridine, the additional examples in Table 2 were prepared using the method illustrated above in Example 1.

The starting materials are either commercially available or were prepared according to the literature reference (cited in Table 2) or were prepared as described below:

TABLE 2

| Compd no. | cyanotoluene (lit. Reference) | amine (lit reference) | MS (MH)$^+$ | NMR δ (d$_6$-DMSO) |
|---|---|---|---|---|
| 9 | 3-cyanobenzylbromide ex. Aldrich | 2-n-Butylbenzimidazole JACS (1937), 59 178 | 467 | 0.9(3H, t), 1.3(2H, m), 1.7(2H, m) 3.17(2H, t), 5.82(2H, s), 6.3(2H, s), 7.2(1H, d), 7.32(1H, d), 7.57(5H, m), 7.81(2H, d), 7.98(1H, s), 8.0(2H, d); |
| 10 | 4-cyanobenzylbromide ex. Aldrich | 2-methylaminopyridine ex. Aldrich | 401 | 3.2(3H, s), 4.97(2H, s), 6.3(2H, s), 6.9(1H, t), 7.2(2H, t), 7.41(2H, d), 7.5(1H, t), 7.6(1H, t), 8.0(5H, m); |
| 12 | 4-cyanobenzylbromide ex. Aldrich | indoline ex. Aldrich | 412 | 2.88(2H, t), 3.25(2H, t), 4.32(2H, s), 6.3(2H, s), 6.57(2H, m), 6.97(1H, t), 7.02(1H, d), 7.2(1H, d), 7.57(4H, m), 8.0(3H, m); |

TABLE 2-continued

| Compd no. | cyanotoluene (lit. Reference) | amine (lit reference) | MS (MH)+ | NMR δ (d₆-DMSO) |
|---|---|---|---|---|
| 15 | 4-cyanobenzylbromide ex. Aldrich | 2-n-Butylbenzimidazole JACS (1937), 59 178 | 467 | 0.8(3H, t), 1.32(2H, m), 1.66(2H, m), 2.8(2H, t), 5.53(2H, s), 6.3(2H, s), 7.1(3H, d), 7.2(2H, d), 7.5(4H, m), 7.97(3H, m); |
| 16 | 4-cyanobenzylbromide ex. Aldrich | [structure: imidazo[4,5-b]pyridine with butyl] Tetrahedron (1992) 48(48) 10549 | 468 | 0.88(3H, t), 1.32(2H, m), 1.8(2H, m), 3.02(2H, t), 6.1(2H, s), 6.3(2H, s), 7.2(1H, d), 7.5(1H, t), 7.6(1H, t), 7.63(2H, d), 7.78(1H, t), 8.0(3H, m), 8.61(1H, d), 9.0(1H, d); |
| 21 | 3-cyanobenzylbromide ex. Aldrich | 2-methylaminopyridine ex. Aldrich | 401 | 5.0(2H, s), 6.3(2H, s), 6.83(1H, t), 7.1(1H, m), 7.22(1H, d), 7.39(1H, d), 7.6(3H, m), 7.82(1H, t), 7.98(3H, m), 8.03(1H, d); |
| 22 | 3-cyanobenzylbromide ex. Aldrich | benzimidazole ex. Aldrich | 411 | 5.8(2H, s), 6.3(2H, s), 7.2(1H, d), 7.57(6H, m), 7.85(2H, m), 8.0(2H, m), 8.19(1H, d), 9.7(1H, s); |
| 24 | 2-methoxy-4-cyanotoluene JCS (C), (1969) 183 | benzimidazole ex. Aldrich | 441 | 3.9(3H, s), 5.7(2H, s), 6.3(2H, s), 7.2(1H, d), 7.6(7H, m), 7.85(2H, m), 7.98(1H, d), 9.6(1H, s); |
| 26 | 4-cyanobenzylbromide ex. Aldrich | 2-Methylaminobenzoxazole JCS (1934) 1186–1190 | 441 | 3.1(3H, s), 4.8(2H, s), 6.3(2H, s), 7.0(1H, t), 7.13(1H, t), 7.22(1H, d), 7.28(1H, d), 7.4(1H, d), 7.5(2H, d), 7.57(2H, t), 8.0(3H, m); |
| 27 | 4-cyanobenzylbromide ex. Aldrich | 2-methylamino-5-bromopyridine JOC (1983) 48 1064 | 479/481 | 3.05(3H, s), 4.82(2H, s), 6.3(2H, s), 6.7(1H, d), 7.2(1H, d), 7.35(2H, d), 7.57(2H, m), 7.68(1H, dd), 7.95(3H, m), 8.13(1H, d); |
| 29 | 4-cyanobenzylbromide ex. Aldrich | 2-methylamino-5-phenylpyridine Heterocyles (1986) 24 (7), 1815 | 477 | 3.25(3H, s), 5.0(2H, s), 6.3(2H, s), 7.2(2H, m), 7.39(1H, t), 7.5(6H, m), 7.65(2H, d), 8.0(3H, t), 8.18(1H, t), 8.3(1H, s); |
| 38 | 2-methoxy-4-cyanotoluene JCS (C), (1969) 183 | 2-methylamino-5-phenylpyridine Heterocyles (1986) 24 (7), 1815 | 507 | 3.2(3H, s), 3.9(3H, s), 4.85(2H, s), 6.3(2H, s), 7.1(1H, m), 7.2(1H, d), 7.25(1H, d), 7.35(1H, d), 7.46(3H, m), 7.6(5H, m), 7.98(1H, d), 8.5(1H, d), 8.26(1H, s); |
| 39 | 2-methoxy-4-cyanotoluene JCS (C), (1969) 183 | 2-aminopyridine ex. Aldrich | 417 | 3.9(3H, s), 4.6(2H, s), 6.3(2H, d), 6.8(1H, m), 7.1(2H, m), 7.5(5H, m), 7.9(3H, m) |
| 41 | 2-bromo-4-cyanotoluene J. Prakt. Chem. (1889) 39 487 | 2-methylaminopyridine ex. Aldrich | 479/481 | 4.9(2H, s), 6.32(2H, s), 6.85(1H, m), 7.0(1H, m), 7.25(2H, m), 7.56(2H, m), 7.83(1H, m), 7.98(2H, m), 8.05(1H, d), 8.2(1H, s); |
| 13 | 4-cyanobenzylbromide ex. Aldrich | benzimidazole ex. Aldrich | 411 | 5.8(2H, s), 6.3(2H, s), 7.2(1H, d), 7.55(6H, m), 7.82(2H, m), 8.0(3H, m), 9.68(1H, s); |
| 14 | 4-cyanobenzylbromide ex. Aldrich | indoline ex. Aldrich | 410 | 5.45(2H, s), 6.3(2H, s), 6.48(1H, s), 7.02(2H, m), 7.2(1H, s), 7.3(2H, d), 7.4(1H, d), 7.5(4H, m), 7.95(3H, br d); |
| 40 | 4-cyanobenzylbromide ex. Aldrich | 2-n-butylaminopyridine Hererocycles (1988) 27 319 | 443 | 0.85(3H, t), 1.3(2H, m), 1.5(2H, m), 3.45(2H, t), 4.8(2H, s), 6.34(2H, s), 6.52(2H, m), 7.02(1H, d), 7.35(2H, d), 7.42(3H, m), 7.93(3H, m), 8.05(1H, m); |
| 28 | 3-chloro-4-methylbenzonitrile | 2-methylaminopyridine ex. Aldrich | 435/437 | 3.2(3H, s), 4.95(2H, s), 6.3(2H, s), 6.85(1H, t), 7.03(1H, d), 7.22(1H, d), 7.35(1H, d), 7.5(1H, t), 7.58(1H, t), 7.83(1H, br t), 7.92(1H, d), 7.98(1H, d), 8.05(2H, m); |

Example 3

2-(2-Carboxybenzyl)-5-[3-methoxy-4-(N-tert-butoxycarbonyl-N-methyl)aminomethyl] phenyltetrazole (Compound 45 in Table 1)

Step 1
2-(2-Carboethoxybenzyl)-5-[3-methoxy-4-(N-methyl)aminomethyl]phenyltetrazole

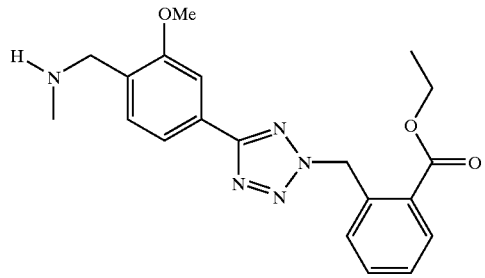

2-(2-Carboethoxybenzyl)-5-(4-bromomethyl-3-methoxy)phenyltetrazole (15.53 g, 36.0 mmol) was stirred in a solution of methylamine in ethanol (33% w/v) (175 ml) at −5° C. for 30 minutes. The solution was warmed to 0° C. for 1 hour before being concentrated under reduced pressure. The residue was partitioned between water and dichloromethane. The dichloromethane was washed with water before being dried over magnesium sulphate and filtered. The organic phase was concentrated under reduced pressure to afford the title compound (10.25 g, 75%) as an orange oil, which was used without further purification. NMR $d_H$ (CDCl$_3$) 1.4 (3H, t), 2.5 (3H, s), 4.0 (3H, s), 4.1 (2H, s), 4.4 (2H, q), 6.3 (2H, s), 6.9 (1H, d), 7.5 (3H, m), 7.7 (2H, m), 8.1 (1H, m). MS [MS]$^+$ 382

Step 2
2-(2-Carboethoxybenzyl)-5-[3-methoxy-4-(N-tert-butoxycarbonyl-N-methyl)aminomethyl]phenyltetrazole

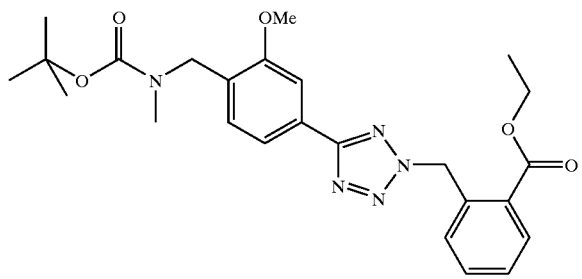

Di-tert-butyl dicarbonate (126 mg, 0.58 mmol) was added to a solution of 2-(2-Carboethoxybenzyl)-5-[3-methoxy-4-(N-methyl)aminomethyl]phenyltetrazole (200 mg, 0.52 mmol) and triethylamine (0.08 ml, 0.58 mmol) in dichloromethane (5 ml). The mixture was stirred at ambient temperature for 2 hours. Water (5 ml) was added, and the mixture was extracted with dichloromethane. The organic phase was dried over magnesium sulfate, filtered and concentrated under reduced pressure. The residue was purified by flash column chromatography using a Varian silica megabondelut column, using ethyl acetate-isohexane (1:9) as the eluent, to yield the title compound (132 mg, 52%) as a colourless oil. NMR $d_H$ (CDCl$_3$) 1.4 (12H, m), 2.9 (3H, br), 3.9 (3H, s), 4.4 (2H, q), 4.5 (2H, br), 6.3 (2H, s), 6.9 (1H, d), 7.2 (1H, m), 7.4 (2H, m), 7.6 (2H, s), 7.7 (1H, d), 8.1 (1H, dd). MS [MS]$^+$ 482

Step 3
Compound 45
2-(2-Carboethoxybenzyl)-5-[3-methoxy-4-(N-tert-butoxycarbonyl-N-methyl)aminomethyl]phenyltetrazole (132 mg, 0.27 mmol) was dissolved in ethanol (4 ml) containing aqueous 1.0 M lithium hydroxide (0.55 ml, 0.55 mmol). The mixture was heated under reflux for 1 hour before the addition of c.HCl (0.11 ml). The solution was concentrated under reduced pressure and the residue was dried, on azeotroping with toluene, to afford the title compound (102 mg, 76%) as a yellow solid. NMR $d_H$ (d$_6$-DMSO) 1.4 (9H, m), 2.8 (3H, s), 3.9 (3H, s), 4.4 (2H, s), 6.3 (2H, s), 7.2 (3H, m), 7.6 (3H, m), 8.0 (1H, m). MS [MH]$^+$ 454

Example 4

Using the appropriate chloride precursor in place of t-butylchloroformate in Example 2, the additional examples in Table 3 were prepared using the method of Example 3.

TABLE 3

| Compd no. | precursor | (MH)$^+$ | NMR δ (d$_6$-DMSO) |
|---|---|---|---|
| 46 | ![structure] ex. Aldrich | 522 | 2.3(3H, s), 3.9(5H, m), 4.8(2H, s), 6.3(2H, s), 6.9–7.7(10H, m), 8.0(1H, m) |
| 47 | ![structure] ex. Aldrich | 478 | 1.0–1.8(13H, m), 2.2(3H, s), 3.9(3H, m), 4.5(2H, d), 6.3(2H, s), 7.2(3H, m), 7.6(3H, m), 8.0(1H, m) |
| 11 | ![structure] ex. Aldrich | 454 | |

Example 5

2-[[5-[4-[[6-[(Butoxycarbonyl)amino]-1H-indol-1-yl]methyl]-3-methoxyphenyl]-2H-tetrazol-2-yl] methyl]-benzoic acid (Compound 1 in Table 1)

Step 1
A mixture of Carbamic acid, [1-[[2-methoxy-4-(1H-tetrazol-5-yl)phenyl]methyl]-1H-indol-6-yl]-, butyl ester (150 mg.0.36 mmol), ethyl(2-bromomethyl)benzoate (104 mg.0.43 mmol), potassium carbonate (60 mg.0.43 mmol) and potassium iodide(10 mg) in acetone (20 ml.) was heated and stirred at 60° C. for 4 hours. The mixture was filtered and the filtrate was evaporated. The residue was dissolved in ethyl acetate and washed twice with water, dried(MgSO$_4$) and evaporated. The resulting oil was columned (Varian Megabondelut silica) run in a gradient of 100% dichloromethane to 80% dichloromethane/20% ethyl acetate. Two isomers were isolated:—the least polar—2-tetrazole) (100 mg.) NMR d(CDCl$_3$)0.95(t,3H),1.2(t,3H),1.4(m,2H),1.6(m, 2H),3.4(m,1H), 3.95(s,3H),4.15(t,2H),4.4(m,2H),5.3(s,2H), 6.3(s,2H),6.5(d,1H),6.65(m,1H),6.8(d,1H),6.9(m,2H), 7.1(d,1H),7.4(m,3H),7.65(m,2H),8.05(m,1H)MS583[MH]$^+$
and the most polar—(1-tetrazole) (20 mg.) NM d(CDCl$_3$) 0.95(t,3H),1.2(t,3H),1.4(m,2H),1.6(m,2H),3.4(m,1H), 3.8(s,3H),4.15(t,2H),4.4(m,2H),5.3(s,2H),6.1(s,2H),6.5(d,1H), 6.65(m,1H),6.8(d,1H),6.9(m,2H),7.1(d,1H),7.4(m,3H),7.65(m,2H),8.05(m,1H)MS583[MH]$^+$ Step 2

A mixture of the 2-(ethyl 2-benzyl carboxylate)tetrazole (the least polar product from step 1) (100 mg, 0.17 mmol) and 1M aqueous lithium hydroxide (1 ml, 1 mmol) in ethanol(10 ml.) was stirred at ambient temperature for 8 hours. The mixture was then acidified to pH1 using 2M hydrochloric acid and after dilution with water, the solid precipitate was collected and washed. (32 mg.) NMR d methyl]-1H-indol-6-yl]-, butyl ester, used in Example 5, the Compounds listed in Table 4 were prepared using a method analogous to that of Example 5

The tetrazole precursors were prepared according to the literature ((1) Yee, Ying K; Bernstein, Peter R.; Adams, Edward J.; Brown, Frederick J.; Cronk, Laura A.; Hebbel, Kevin C.; Vacek, Edward P.; Krell, Robert D.; Snyder, David W. A novel series of selective leukotriene antagonists: exploration and optimization of the acidic region in 1,6-disubstituted indoles and indazoles. J. Med. Chem (1990), 33(9), 2437–51; (2) Brown, Frederick Jeffrey, Bernstein, Peter Robert; Yee, Ying Kwong. Heterocyclic amides. Eur. Pat. Appl. EP179619 A1) or were prepared as described below:

TABLE 4

| Compound No | precursor | MS (MH)$^-$ | NMR δ (d$_6$-DMSO) |
|---|---|---|---|
| 5 | | 566 | (CDCl3) 1.8(m, 8H), 3.7(s, 3H), 4.0(s, 2H), 4.05(m, 1H), 5.6(s, 2H), 6.85(m, 4H), 7.4(m, 1H), 7.6(m, 3H), 8.0(m, 3H) |
| 6 | | 565 | 1.0(m, 2H), 1.15(m, 4H), 1.2(m, 2H), 3.2(s, 3H), 3.7(m, 3H), 6.0(s, 2H), 6.8(m, 2H), 7.2(m, 8H), 7.5(m, 1H), 7.7(m, 1H) |

(d$_6$-DMSO) (0.9(t,3H),1.4(m,2H),1.6(m,2H),3.95(s,3H),4.0(m,2H),5.3(s,2H), 6.3(s,2H),6.4(m,1H),6.8(m,1H),7.0(m,1H),7.2(m,1H),7.35(m,1H),7.4(m,1H), 7.6(m,5H),8.0(m,1H),9.4(s,1H).MS553[MH]$^-$

Example 6

2-[[5-[4-[[6-[(Butoxycarbonyl)amino]-1H-indol-1-yl]methyl]-3-methoxyphenyl]-1H-tetrazol-1-yl]methyl]-benzoic acid (Compound no 2 in Table 1) A mixture of the 1-(ethyl 2-benzyl carboxylate)tetrazole (the most polar isomer produced in Example 5 step 1) (20 mg, 0.034 mmol) and 1M aqueous lithium hydroxide (0.2 ml, 0.2 mmol) in ethanol(2 ml.) was stirred at ambient temperature for 8 hours. The mixture was then acidified to pH1 using 2M hydrochloric acid and after dilution with water, the solid precipitate was collected and washed. (6 mg.).MS553[MH]$^-$

Example 7

Using the appropriate tetrazole precursor in place of the carbamic acid, [1-[[2-methoxy-4-(1H-tetrazol-5-yl)phenyl]

Example 8

1-(2-carboxybenzyl)-3-(3-bromo-4-methyl-N-2-pyridyl)aminomethyl)phenylpyrazole (Compound 43 in Table 1)

Step 1
5-(3-bromo-4-methyl)phenyltetrazole

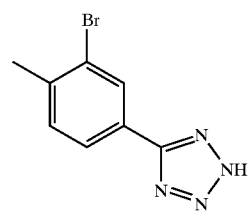

A mixture of 3-bromo-4-methylbenzonitrile (8.8 g, 45 mmol), triethylamine hydrochloride (9.3 g, 67.5 mmol) and sodium azide (8.8 g, 135 mmol) in 1-methyl-2-pyrrolidinone (60 ml) was stirred at 150° C. for 3 hours. The reaction mixture was cooled to ambient temperature and acidified with 2M hydrochloric acid. After stirring for 15 minutes, the mixture was filtered and the residue washed with water and dried to give the title compound (9.2 g). NMR d (d$_6$-DMSO) 2.4 (3H, s), 7.58 (1H, d), 7.95 (1H, d), 8.2 (1H, s); MS [MH]$^+$ 239/241.

Step 2

1-vinyl-5-(3-bromo-4-methyl)phenyltetrazole

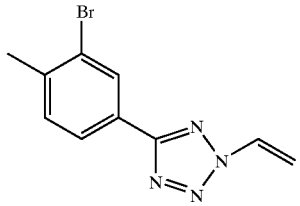

A mixture of 5-(3-bromo-4-methyl)phenyltetrazole (2.4 g, 10 mmol), mercuric acetate (50 mg) and 2 drops of concentrated sulphuric acid in vinyl acetate (8.0 ml) was heated under reflux for 2 hours. The excess vinyl acetate was then evaporated under reduced pressure, and the residue was purified by flash column chromatography on a Varian 20 g silica megabondelut column, eluting with 5% v/v ethyl acetate in isohexane, to give the title compound (2.0 g) NMR d (d$_6$-DMSO) 2.5 (3H, s), 5.4 (1H, dd), 6.25 (1H, dd), 7.37 (1H, d), 7.55 (1H, q), 8.02 (1H, dd), 8.39 (1H, s); MS [MH]$^+$265/267.

Step 3

3-(3-bromo-4-methyl)phenylpyrazole

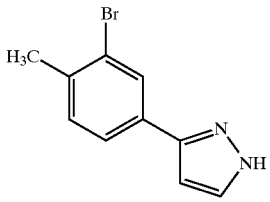

1-vinyl-5-(3-bromo-4-methyl)phenyltetrazole was heated under reflux in 2-dichlorobenzene (60 ml) for 8 hours. The dichlorobenzene was then removed under reduced pressure and the residue was purified by flash column chromatography on a 50 g silica Isolute column, eluting with ethyl acetate, to give the title compound (1.7 g). NMR d (d$_6$-DMSO) 2.32 (3H, s), 6.74 (1H, s), 7.38 (1H, d), 7.7 (2H, m), 8.0 (1H, s), 12.9 (1H, br); MS [MH]$^+$ 237/239.

Step 4

1-(2-carboethoxybenzyl)-3-(3-bromo-4-methyl)phenylpyrazole

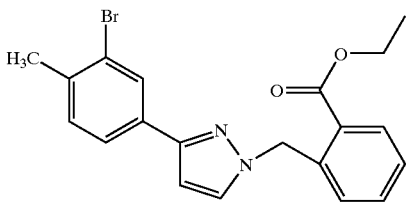

A mixture of 3-(3-bromo-4-methyl)phenylpyrazole (1.7 g, 7.17 mmol), 2-carboethoxybenzyl bromide (1.74 g, 7.17 mmol) and potassium carbonate (4.9 g, 35.8 mmol) in acetone (50 ml) was stirred under reflux for 16 hours. A further 0.87 g (3.59 mmol) of 2-carboethoxybenzyl bromide was added and mixture stirred under reflux for a further 24 hours. The acetone was removed by distillation under reduced pressure and the residue was partitioned between water and ethyl acetate. The ethyl acetate extract was dried over anhydrous magnesium sulphate, filtered and evaporated. The residue was purified by flash column chromatography on a 20 g Varian silica megabondelut column, eluting with 5% v/v to 10% v/v ethyl acetate in isohexane, to leave the title compound (2.2 g). NMR d (d$_6$-DMSO) 1.35 (3H, t), 2.37 (3H, s), 4.34 (2H, q), 5.7 (2H, ), 5.79 (1H, d), 6.85 (1H, d), 7.33 (1H, d), 7.4 (1H, t), 7.5 (1H, t), 7.64 (1H, d), 7.81 (1H, d), 7.9 (1H, d), 7.97 (1H, d); MS [MH]$^+$ 399/401.

Step 5

1-(2-carboethoxybenzyl)-3-(3-bromo-4-bromomethyl)phenylpyrazole

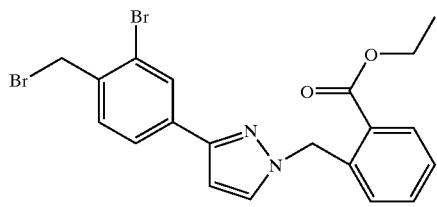

A mixture of 1-(2-carboethoxybenzyl)-3-(3-bromo-4-methyl)phenyltetrazole (2.1 g, 5.26 mmol), N-bromosuccinimide (1.07 g, 6.0 mmol) and benzoyl peroxide (100 mg) in carbon tetrachloride (50 ml) was stirred under reflux for 16 hours. The mixture was cooled and washed with water (3×20 ml), dried over anhydrous magnesium sulphate, filtered and evaporated to leave the crude product as a solid (3.1 g). NMR d (d$_6$-DMSO) 1.34 (3H, t), 4.35 (2H, q), 4.75 (2H, s), 5.72 (2H, s), 6.83 to 8.0 (9H, aromatics); MS [MH]$^+$ 477/479/481

Step 6

1-(2-carboethoxybenzyl)-3-(3-bromo-4-methylaminomethyl)phenylpyrazole

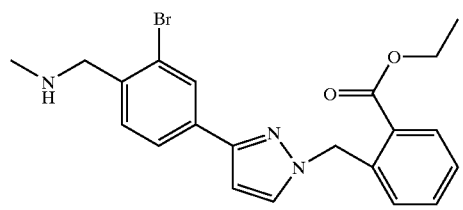

1-(2-carboethoxybenzyl)-3-(3-bromo-4-bromomethyl)phenyltetrazole (1.1 g) was stirred in 33% ethanolic methylamine solution (50 ml) for 6 hours. The ethanol was removed by evaporation and the residue was partitioned between ethyl acetate and saturated sodium carbonate solution. The ethyl acetate extract was dried over anhydrous magnesium sulphate, filtered and evaporated to an oil. This oil was purified by flash column chromatography on a Varian 20 g silica megabondelut column, eluting with ethyl acetate followed by 10% ethanol in ethyl acetate and finally 10% ethanol in ethyl acetate containing 1% of triethylamine, to give the product (290 mg). NMR d (d$_6$-DMSO) 1.4 (3H, t), 2.42 (3H, s), 3.82 (2H, s), 4.4 (2H, q), 5.8 (2H, s), 6.59 (1H, d), 6.9 (1H, d), 7.4 (4H, m), 7.7 (1H, dd), 8.01 (2H, m); MS [MH]$^+$ 477/479/481

Step 7
1-(2-carboethoxybenzyl)-3-[3-bromo-4-(N-methyl-N-2-pyridyl)aminomethyl]pyrazole

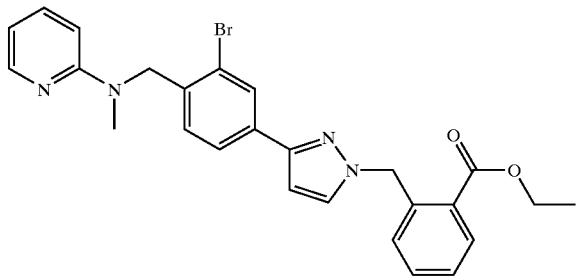

A mixture of 1-(2-carboethoxybenzyl)-3-(3-bromo-4-methylaminomethyl)phenyltetrazole (280 mg, 0.65 mmol) and N,N-diisopropylamine (0.5 ml) in 2-fluoropyridine (10 ml) was stirred under reflux in an inert atmosphere for 48 hours. The excess 2-fluoropyridine was evaporated under reduced pressure and the residue was partitioned between ethyl acetate and saturated sodium carbonate solution. The ethyl acetate extract was dried over anhydrous magnesium sulphate, filtered and evaporated to dryness. The residue was purified by flash column chromatography on a Varian 20 g silica megabondelut column, eluting with 20% ethyl acetate in isohexane, to give the title compound (200 mg). NMR d ($d_6$-DMSO) 1.4 (3H, t), 3.15 (3H, s), 4.4 (2H, q), 4.8 (2H, s), 5.8 (2H, s), 6.43 (1H, d), 6.58 (2H, m), 6.85 (1H, d), 7.07 (1H, d), 7.4 (4H, m), 7.62 (1H, d), 8.01 (1H, d), 8.03 (1H, s), 8.19 (1H, d); MS $[MH]^+$ 505/507.

Step 8
(Compound 43)

A mixture of 1-(2-carboethoxybenzyl)-3-[3-bromo-4-(N-methyl-N-2-pyridyl)aminomethyl]phenylpyrazole (190 mg, 0.375 mmol) and 2M aqueous lithium hydroxide solution (0.5 ml, 0.5 mmol) in ethanol (10 ml) was stirred under reflux for 2 hours. The mixture was cooled to ambient temperature and neutralised with 1M aqueous hydrochloric acid. The solution was concentrated under reduced pressure. The residue was purified by flash column chromatography on a Varian 20 g silica megabondelut eluting with 5% v/v to 10% v/v ethyl acetate in isohexane to obtain the title compound (140 mg). NMR d ($d_6$-DMSO) 3.03 (3H, s), 4.79 (2H, s), 5.75 (2H, s), 6.6 (2H, m), 6.78 (2H, m), 7.0 (1H,d), 7.39 (1H, t), 7.5 (2H, m), 7.66 (1H, d), 7.82 (1H, d), 7.9 (1H, d), 8.0 (1H, s), 8.03 (1H, d); MS $[MH]^+$ 477/479.

Example 9

Preparation of Compound 36 in Table 1—1-(2-Carboxy)benzyl-3-[3-chloro-4-(N-methyl-N-2-pyridyl)aminomethyl]phenylpyrazole Step 1
5-(3-Chloro-4-methyl)phenyltetrazole

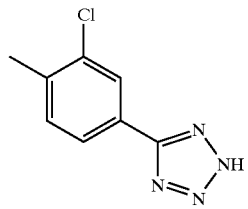

3-Chloro-4-methylbenzonitrile (1.51 g, 10 mmol) was dissolved in N-methylpyrrolidione (20 ml) containing tri-ethylamine hydrochloride (2.05 g, 15 mmol) and sodium azide (1.95 g, 30 mmol). The solution was heated at 155° C. for 5 hours before being cooled and diluted with water (40 ml). The mixture was acidified using dilute hydrochloric acid (3.0 M, 20 ml). The precipitate formed was filtered off and washed with water before being dried to yield the title compound (2.05 g) which was used without further purification. MS $[MH]^+$ 195 NMR $d_H$ ($d_6$-DMSO) 2.4 (3H, s), 7.6 (1H, d), 7.9 (1H, d), 8.0 (1H, s).

Step 2
2-Vinyl-5-(3-chloro-4-methyl)phenyltetrazole

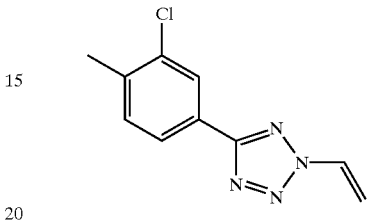

5-(3-Chloro-4-methyl)phenyltetrazole (582 mg, 3 mmol), was dissolved in vinyl acetate (2.5 ml) containing mercury (II) acetate (20 mg) and catalytic concentrated sulfuric acid (1 drop). The mixture was heated, under argon, at 100° C. for approximately 16 hours before being cooled. The mixture was purified by flash column chromatography, using ethyl acetate-iso-hexane (10:90) as eluent, to afford the title compound (530 mg, 80%). MS $[MH]^+$ 220 NMR $d_H$ ($d_6$-DMSO) 2.4 (3H, s), 5.6 (1H, d), 6.2 (1H, d), 7.5 (1H, d), 7.9 (2H, m), 8.0 (1H, s).

Step 3
3-(3-chloro-4-methyl)phenylpyrazole

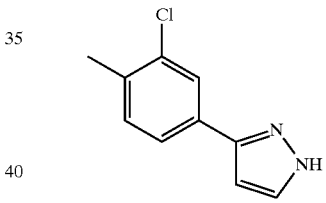

2-Vinyl-5-(3-chloro-4-methyl)phenyltetrazole (370 mg, 1.7 mmol) was heated at 180° C. in 1,2-dichlorobenzene (25 ml) for approximately 16 hours. The mixture was concentrated under reduced pressure to afford the title compound (246 mg, 76%) as a pink solid. MS $[MH]^+$ 193 NMR $d_H$ ($d_6$-DMSO) 2.3 (3H, s), 6.7 (1H, s), 7.3 (1H, d), 7.7 (2H, m), 7.8 (1H, s), 12.9 (1H, br).

Step 4
1-(2-Carbomethoxy)benzyl-3-(3-chloro-4-methyl)phenylpyrazole

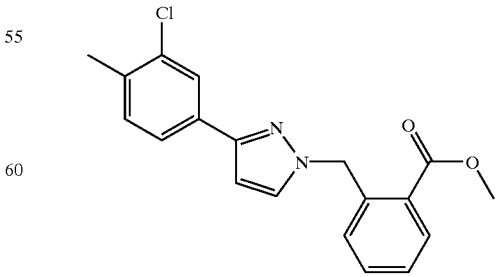

3-(3-Chloro-4-methyl)phenylpyrazole (230 mg, 1.2 mmol) was dissolved in acetone (5 ml) containing 2-carbomethoxybenzyl bromide (365 mg, 1.6 mmol), potassium carbonate (200 mg) and potassium iodide (catalytic). The mixture was heated at 60° C. for approximately 16 hours before being concentrated under reduced pressure. The residue was purified by flash column chromatography, using ethyl acetate-iso-hexane (10:90 increasing to 25:75) as eluent, to yield the title compound (326 mg, 80%). MS [MH]+ 341 NMR $d_H$ ($d_6$-DMSO) 2.3 (3H, s), 3.9 (3H, s), 5.7 (2H, s), 6.8 (1H, d), 6.9 (1H, d), 7.3 (1H, m), 7.4 (1H,m), 7.5 (1H, m), 7.6 (1H, m), 7.8 (1H, s), 7.9 (2H, m).

Step 5
1-(2-Carbomethoxy)benzyl-3-(3-chloro-4-bromomethyl)phenylpyrazole

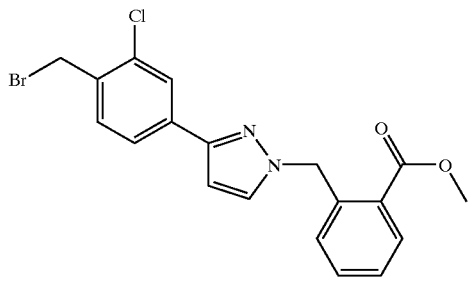

1-(2-Carbomethoxy)benzyl-3-(3-chloro-4-methyl)phenylpyrazole (320 mg, 0.9 mmol) was taken up in carbon tetrachloride (10 ml) containing N-bromosuccinimide (184 mg, 1.0 mmol). The mixture was heated to 70° C. and AIBN (20 mg) was added. The temperature was increased to 90° C. for 4.5 hours and the solution was cooled and filtered. The filtrate was washed with water and the organic phase was dried with magnesium sulfate, filtered and concentrated under reduced pressure to afford the title compound (600 mg) which was used without further purification. MS [MH]+ 421.

Step 6
1-(2-Carbomethoxy)benzyl-3-[3-chloro-4-(N-methyl-N-2-pyridyl)aminomethyl]phenylpyrazole

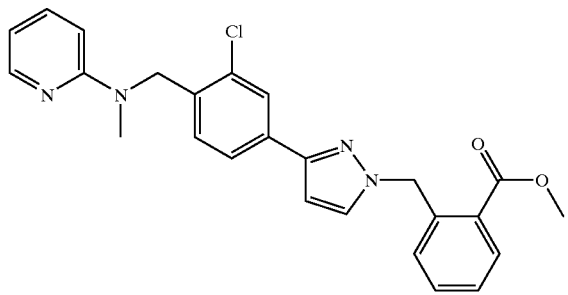

1-(2-Carbomethoxy)benzyl-3-(3-chloro-4-bromomethyl)phenylpyrazole (600 mg, 1.4 mmol) was added to a solution of 2-(N-methyl)aminopyridine (0.14 ml, 1.4 mmol) containing potassium carbonate (386 mg) and catalytic potassium iodide. The mixture was stirred at ambient temperature for approximately 16 hours before being poured onto water. The mixture was extracted using diethyl ether and the combined organic extracts were washed with water and brine before being dried over magnesium sulfate and filtered. The solution was concentrated under reduced pressure. The residue was purified by flash column chromatography, using ethyl acetate-iso-hexane (10:90 increasing to 25:75) as eluent, to afford the title compound (30 mg, 5%). MS [MH]+ 447.

Step 7
Compound 36
1-(2-Carbomethoxy)benzyl-3-[3-chloro-4-(N-methyl-N-2-pyridyl)aminomethyl]phenylpyrazole (28 mg, 0.06 mmol) was stirred in a solution of aqueous sodium hydroxide (1.0 M, 0.5 ml) and methanol (3 ml) at ambient temperature for approximately 16 hours. The methanol was removed under reduced pressure, and the aqueous residue was washed using ethyl acetate. The aqueous phase was acidified using dilute hydrochloric acid (1.0 M) and the resulting solution was extracted into diethyl ether. The extracts were dried over magnesium sulfate, filtered and concentrated under reduced pressure to afford the title compound (22 mg, 81%) as a solid. MS [MH]+ 431 NMR $d_H$ ($d_6$-DMSO) 3.1 (3H, s), 4.9 (2H, s), 5.8 (2H, s), 6.7 (2 H, m), 6.9 (2H, m), 7.1 (1H, d), 7.4 (1H, m), 7.6 (2H, m), 7.7 (1H, m), 7.9 (2H, m), 8.0 (1H, m), 8.1 (1H, m).

Example 10

Using a method analogous to that described in Examples 8 and 9, the compounds listed in Table 5 were prepared.

TABLE 5

| Example | ester precursor* | MS (MH)+ | NMR δ ($d_6$-DMSO) |
|---|---|---|---|
| 17 | Ethyl | 463 | 0.8 (3H, t), 1.3 (2H, m), 1.7 (2H, m), 2.8 (2H, t), 5.4 (2H, s), 5.7 (2H, s), 6.7 (2H, m), 7–7.8 (12H, m). |
| 25 | Methyl | 397 | 3.1 (3H, s), 4.8 (2H, s), 5.8 (2H, s), 6.7 (4H, m), 7.3 (2H, d), 7.5 (3H, m), 7.8 (2H, d), 7.9 (1H, m), 8.0 (1H, d), 8.1 (1H, m). |
| 19 | Ethyl | 549 | 0.8 (6H, m), 1.1–1.6 (8H, m), 2.2 (1H, m), 5.3 (2H, s), 5.7 (2H, s), 6.4 (1H, m), 6.7 (2H, m), 7.1 (3H, m), 7.4 (4H, m), 7.8 (5H, m), 9.7 (1H, s). |

*Ethyl ester precursors followed the route of Example 8 whilst methyl ester precursors followed the route of Example 9.

Example 11

1-(2-carboxybenzyl)-4-(3-methoxy-4-(N-methyl-N-2-pyridyl)aminomethyl)phenylpyrazole (Compound 44 in Table 1)

Step 1
(N-methyl-N-2-pyridyl)-2-methoxy-4-iodobenzamide

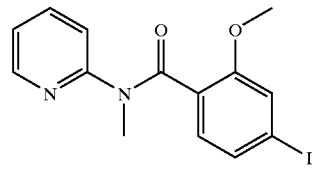

4-iodo-2-methoxybenzoic acid (2.5 g, 9 mmol) dissolved in 25 ml dichloromethane and 2 drops dimethylformamide was treated with oxalyl chloride (1.66 ml, 19 mmol) in five 0.33 ml portions over 15 minutes waiting for the effervescence to subside between additions. The reaction mixture was evaporated to dryness and the residue dissolved in dichloromethane (15 ml). This solution was added dropwise to a solution of 2-methylaminopyridine (972 mg, 9 mmol) and triethylamine (2.51 ml, 18 mmol) in dichloromethane (20 ml). The reaction was allowed 1 hour, washed with water twice and evaporated down to an oil. The crude oil was eluted down a 20 g Varian MegaBond Elut® column using 20–30% v/v ethyl acetate in isohexane. The product containing fractions were grouped and evaporated to an oil which solidified on standing. The resulting solid was dried under high vacuum (3.12 g): NMR δ (CDCl$_3$) 3.51 (3 H, s) 3.62 (3 H, s) 7.04 (4 H, m) 7.26 (1H, d) 7.47 (1 H, t) 8.39 (1 H, d); MS [MH$^+$] 369.1

Step 2

1-iodo-3-methoxy-4-(N-methyl-N-2-pyridyl)aminomethylbenzene

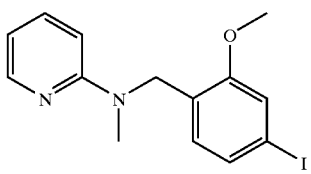

Trichlorosilane (0.5 mL 4.95 mmol) disolved in 2 ml toluene was added to (N-methyl-N-2-pyridyl)-2-methoxy-4-iodobenzamide (300 mg, 0.815 mmol) in 2 ml toluene under an argon atmosphere. The reaction was refluxed for 20 hours, cooled, diluted with dichloromethane and gently treated with water until effervescence subsided. The mixture was then basified with solid KOH to pH 13, the phases separated and the aqueous extracted with dichloromethane twice. The combined organic extracts were evaporated to an oil (285 mg at 100% strength): NMR δ (CDCl$_3$) 3.1 (3 H, s) 3.83 (3 H, s) 4.67 (2 H, s) 6.44 (1 H, d) 6.53 (1 H, dd) 6.74 (1 H, d) 7.18 (2 H, m) 7.4 (1 H, m) 8.17 (1 H, dd); MS [MH$^+$] 355.2

Step 3

1-pinacolboronate-3-methoxy-4-(N-methyl-N-2-pyridyl)aminomethylbenzene

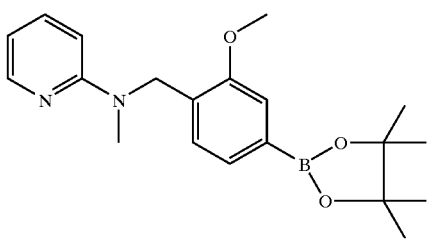

To an argon inerted flask was charged the 1-iodo-3-methoxy-4-(N-methyl-N-2-pyridyl)aminomethylbenzene (87 mg), 0.246 mmol), PdCl$_2$(dppf) (6 mg, 0.0074 mmol) potassium acetate (72.4 mg, 0.737 mmol), bis pinacolato diboron (69 mg, 0.272 mmol) and dimethyl sulphoxide (4 ml). The reaction was heated to 80° C. and after 5 minutes cooled to ambient. The reaction was quenched with water and extracted with dichloromethane 3 times. The combined dichloromethane extracts were washed with water and evaporated to an oil. The oil was eluted down a 10 g Varian Mega Bond Elute column with 5–30% ethyl acetate in isohexane. The product containing fractions were combined and evaporated to an oil (58 mg): NMR δ (CDCl$_3$) 1.33 (12 H, s) 3.16 (3 H, s) 3.9 (3 H, s) 4.73 (2 H, s) 6.43 (1 H, d) 6.51 (1 H, m) 7.05 (1 H, d) 7.33 (3 H, m) 8.16 (1 H, d); MS [MH$^+$] 355.4

Step 4

1-(2-Carboethoxybenzyl)-4-iodopyrazole

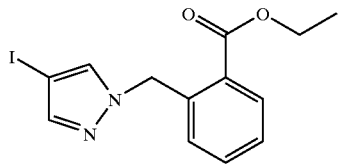

To a solution of ethyl-(2-bromomethyl)benzoate (1.0 g, 4.12 mmol) in dimethylformamide (10 ml) was added potassium carbonate (625 mg, 4.52 mmol), potassium iodide (10 mg, 0.06 mmol) and 4-iodopyrazole (879 mg, 4.53 mmol). The reaction was stirred at ambient for 15 minutes, then at 60° C. for 2 hours. The reaction was cooled down to ambient, filtered, the residues washed with DMF and the combined filtrates evaporated down to an oil. The crude oil was eluted down a 20 g Varian Mega Bond Elut® column with 0–6% ethyl acetate in isohexane. The fractions containing the product were combined and evaporated down to isolate the product as an oil (930 mg): NMR δ (CDCl$_3$) 1.4 (3 H, t) 4.39 (2 H, q) 5.75 (2 H, s) 6.99 (1 H, d) 7.36 (1 H, t) 7.46 (1 H, t) 7.55 (2 H, s) 8.02 (1 H, d); MS [MH$^+$] 357.1

Step 5

1-(2-carboethoxybenzyl)-4-(3-methoxy-4-methyl-N-2-pyridyl)aminomethyl)phenylpyrazole

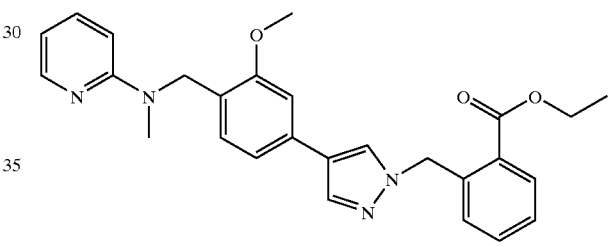

To an argon inerted flask was charged 1-pinacolboronate-3-methoxy-4-(N-methyl-N-2-pyridyl)aminomethylbenzene (58 mg, 0.164 mmol), 1-(2-Carboethoxybenzyl)-4-iodopyrazole (58 mg, 0.164 mmol), potassium carbonate (34 mg, 0.246 mmol), PdCl$_2$(dppf) (2.6 mg, 0.0032 mmol) and dimethylformamide (4 ml). The reaction was stirred at 60° C. for 2.5 hours, cooled to ambient, quenched with water and extracted with dichloromethane 3 times. The combined extracts were washed with water and evaporated to an oil. The crude oil was eluted down a 10 g Varian Mega Bond Elut® column with 5–30% ethyl acetate in isohexane. The product containing fractions were combined and evaporated down to isolate the product as an oil (57 mg): NMR δ (CDCl$_3$) 1.39 (3 H, t) 3.13 (3 H, s) 3.88 (3 H, s) 4.38 (2 H, q) 4.72 (2 H, s) 5.78 (2 H, s) 6.47 (1 H, d) 6.52 (1 H, m) 6.99 (4 H, m) 7.4 (3 H, m) 7.72 (1 H, s) 7.8 (1 H, s) 8.02 (1 H, d) 8.18 (1 H, d); MS [MH$^+$] 457.2

Step 6

(Compound 44)

1-(2-carboethoxybenzyl)-4-(3-methoxy-4-(N-methyl-N-2-pyridyl)aminomethyl)phenylpyrazole (134 mg, 0.29 mmol) and 1M aq lithium hydroxide (0.59 ml, 0.59 mmol) were refluxed in ethanol (5 ml) for 2.5 hours. The reaction mixture was evaporated to dryness and the residue partitioned between dichloromethane and water. 0.96 N hydrochloric acid (0.61 ml, 0.59 mmol) was added to the mixture, the phases stirred and separated. The aqueous phase was extracted with dichloromethane and the combined organic extracts washed with water and then evaporated to a foam which was broken up to a solid (85 mg at 100% strength): NMR δ (CDCl₃) 3.12 (3 H, s) 3.83 (3 H, s) 4.75 (2 H, s) 5.51 (2 H, s) 6.58 (2 H, m) 6.85 (2 H, m) 6.99 (2 H, m) 7.42 (3 H, m) 7.61 (1 H, s) 7.78 (1 H, s) 8.02 (1 H, d) 8.29 (1 H, d); MS [MH⁺] 429.3

Example 12

Preparation of 2-(2-carboxybenzyl)-5-[4-(2-quinolylmethoxy)phenyl]tetrazole (Compound 33 in Table 1)

Step 1
5-(4-hydroxyphenyl)tetrazole

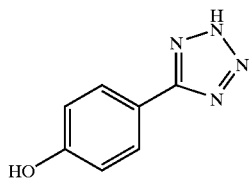

A mixture of 4-cyanophenol (4.8 g, 40 mmol), sodium azide (7.8 g, 120 mmol) and triethylamine hydrochloride (8.24 g, 60 mmol) in 1-methyl-2-pyrrolidinone (40 ml) was stirred and heated in an oil bath at 140° C. for five hours. The cooled solution was acidified with 2M hydrochloric acid (200 ml) and extracted with ethyl acetate (3×100 ml). The combined ethyl acetate extracts were washed with water (3×100 ml), dried over anhydrous magnesium sulphate, filtered and evaporated to a fawn solid which was crystallised from 50% v/v ethyl acetate in isohexane to give the title compound (5.1 g.) NMR d (d₆-DMSO) 6.95 (2H,d), 7.85 (2H,d), 10.13 (1H,br); MS[MH]⁺ 163

Step 2
2-(carboethoxybenzyl)-5-(4-hydroxyphenyl)tetrazole

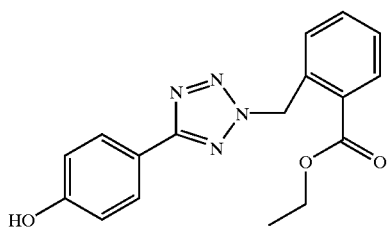

A mixture of 5-(4-hydroxyphenyl)tetrazole (1.62 g, 10 mmol), 2-carboethoxybenzylbromide (2.91 g, 12 mmol) and sodium hydrogen carbonate (1.7 g, 20 mmol) in N,N-dimethylformamide (10 ml) was stirred at ambient temperature for 16 hours. The mixture was then diluted with water (40 ml) and extracted with ethyl acetate (3×20 ml). The ethyl acetate extracts were washed with water (3×20 ml), dried over anhydrous magnesium sulphate, filtered and evaporated to an oil.

This oil was purified by flash chromatography on a Varian 20 g silica megabondelut column eluting with 10% to 40% v/v ethyl acetate in isohexane to give the title compound (2.2 g) as a white solid. NMR d (d₆-DMSO) 1.35 (3H,t), 4.3 (2H,q), 6.3 (2H,s), 6.98 (2H,d), 7.4 (1H,d), 7.65 (1H,t), 7.7 (1H,t), 7.9 (2H,d), 8.02 (1H,d), 10.0 (1H,s); MS[MH]⁺ 325

Step 3
2-(2-carboethoxybenzyl)-5-[4(2-quinolylmethoxy)phenyl] tetrazole

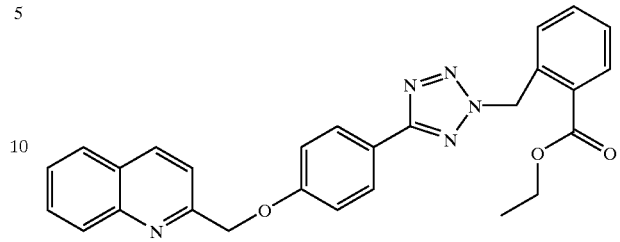

A mixture of 2-(carboethoxybenzyl)-5-(4-hydroxyphenyl)tetrazole (182 mg, 0.56 mmol), 2-chloromethylquinoline hydrochloride (107 mg, 0.5 mmol), potassium carbonate (276 mg, 2.0 mmol) and potassium iodide (20 mg) in N,N-dimethylformamide (3.0 ml) was stirred at ambient temperature for 24 hours. The mixture was diluted with water (20 ml), and aqueous saturated sodium carbonate solution (5.0 ml) was added. The mixture was stirred for 15 minutes then the precipitate was filtered off, washed with water and dried to give the title compound. (200 mg). NMR d (d₆-DMSO) 1.25 (3H,t), 4.25 (2H,q), 5.44 (2H,s), 6.24 (2H,s), 7.22 (2H,d), 7.3 (1H,d), 7.52 (1H,t), 7.6 (2H,m), 7.7(1H,d), 7.78 (1H,t), 7.98 (5H,m), 8.4 (1H,d); MS[MH]⁺ 466

Step 4
Compound 33

A mixture of 2-(2-carboethoxybenzyl)-5-[4-(2-quinolylmethoxyphenyl]tetrazole (150 mg, 0.322 mmol) and 1M aqueous lithium hydroxide (1 ml, 1.0 mmol) in ethanol (5.0 ml) was stirred and heated at reflux temperature for 30 minutes. The mixture was cooled and acidified with concentrated hydrochloric acid (0.5 ml). The precipitate which formed on standing was collected by filtration, washed with ethanol and dried to give the title compound (130 mg) as the hydrochloride salt. NMR d (d₆-DMSO) 5.35 (2H, br), 5.6 (2H, s), 6.3 (2H, s), 7.2 (3H,m), 7.5 (1H,t), 7.6 (1H,t), 7.7(1H,t), 7.8 (1H,d), 7.85 (1H,t), 8.02 (3H,d), 8.1 (1H,d), 8.15 (1H,d), 8.6 (1H,d); MS[MH]⁺ 438

Example 13

Biological Assays
(a) Ligand Binding Assay

The assay was based on a scintillation proximity assay in which the displacement of radiolabelled [³H] BRL 49653 (rosiglitazone) binding from biotinylated human PPARγ-recombinant protein was measured. The PPARγ ligand binding domain (LBD) of human PPARγ1 was expressed in E-Coli as a poly his and c-myc tagged fusion protein. Compounds of the invention were incubated with [³H] BRL 49653, 30 nM (0.1 mCi), biotinylated human PPARg LBD protein (150 ng) and streptavidin SPA beads, 025 mg/well. Compounds were able to displace radiolabel and so have pharmacological potential as PPARγ agonists or antagonists.
(B) Cell Transactivation Assays Assays were performed by transient transfection of Hepa1c1c7 cells in which compounds of the invention were tested for their ability to activate human PPARα, δ and γ isoforms. Cells were co-transfected with either PPARa, d and g expression vectors (containing the entire ORF sequence) and a reporter construct carrying a PPRE linked Lac Z construct. Cells were transfected using Superfect and cultured in T75 flasks overnight, then plated into 96 well plates and left for 5 hours before the addition of test compound. After a further 24 hours PPAR activation was quantitated indirectly as β-Galactosidase activity by hydrolysis of chlorophenol red-β-D-galactopyranoside (CPRG), measured spectrophotometrically at 580 nm. Compounds of the invention were active in this assay. For example Compound 46 in Table 1 at a concentration of 10 μM showed a γ transactivation of 64% and an α transactivation of 25%.

According to their activity in transactivation assays and by comparison to the selective PPARγ agonist, BRL 49653; compounds of the invention were categorised as either having pharmacological properties consistent with: selective PPARγ agonists, partial agonists or non-selective PPAR α/γ agonists.

Adipocyte Differentiation Assay

3T3L1 preadipocytes were grown in DMEM containing 10% NBCS and 1 day post-confluence cells were cultured in differentiation medium (DMEM containing 5% FCS, 1 μg/ml insulin, 0.25 μM dexamethasone and 0.5 mM IBMX) in the presence or absence of compounds. BRL 49653 was used as the positive control and the medium replenished after 3 days. On day 7, cells were lysed and glycerophosphate dehydrogenase activity measured spectrophotometrically at 340 nm. Under the conditions of the assay BRL 49653 induces a dose related increase in glycerophosphate dehydrogenase activity. Compounds of the invention which were found to activate PPARγ in the transactivation assay (vide supra) induced glycerophosphate dehydrogenase activity in 3T3L1 cells in a dose-related manner. For example, Compound 46 in Table 1 at a concentration of 10 μM showed activity at 79% as compared to the control.

What is claimed is:

1. A method for treatment of type 2 diabetes, treatment of insulin resistance syndrome (IRS), treatment of dyslipidemia or reducing the risk of cardiovascular disease comprising administering to a patient in need thereof a therapeutically effective amount of a compound of formula (I)

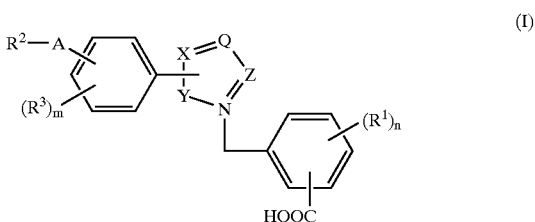

or a pharmaceutically acceptable salt or ester thereof, optionally in combination with a pharmaceutically acceptable excipient, where Q, X, Y and Z are either —$CR^a$=, —$CR^b$=$CR^c$— or —N=; where $R^a$, $R^b$ and $R^c$ are independently selected from hydrogen, halo or a bond, such that together with the nitrogen atom to which Y and Z are attached, they form a five- or six-membered aromatic ring;

$R^1$ and $R^3$ are independently selected from $C_{1-3}$alkyl, halo, halo$C_{1-3}$alkyl, $C_{1-3}$alkoxy, or halo$C_{1-3}$alkoxy;

n and m are independently selected from 0, 1 or 2;

A is an alkylene, alkenylene or alkynylene chain optionally interposed by a heteroatom; and $R^2$ is an optionally substituted aryl, optionally substituted heterocyclyl or optionally substituted cycloalkyl moiety.

2. The method as claimed in claim 1 wherein the group comprising —Y—X—Q—Z— and the nitrogen to which it is attached form a 5-membered aromatic ring.

3. The method as claimed in claim 1 or claim 2, wherein, in the compound of formula I the carboxylic acid group is at the ortho position on the benzyl ring.

* * * * *